(12) United States Patent
Salzman et al.

(10) Patent No.: US 11,466,313 B2
(45) Date of Patent: Oct. 11, 2022

(54) NUCLEIC ACID QUANTIFICATION USING CONCENTRATION-SPECIFIC BARCODES

(71) Applicant: The Board of Trustees of the Leland Stanford Junior University, Stanford, CA (US)

(72) Inventors: Julia Salzman, Palo Alto, CA (US); Peter L. Wang, Menlo Park, CA (US); Caroline Horn, Los Altos, CA (US)

(73) Assignee: THE BOARD OF TRUSTEES OF THE LELAND STANFORD JUNIOR UNIVERSITY, Stanford, CA (US)

(*) Notice: Subject to any disclaimer, the term of this patent is extended or adjusted under 35 U.S.C. 154(b) by 0 days.

(21) Appl. No.: 17/043,539

(22) PCT Filed: Apr. 12, 2019

(86) PCT No.: PCT/US2019/027365
§ 371 (c)(1),
(2) Date: Sep. 29, 2020

(87) PCT Pub. No.: WO2019/200341
PCT Pub. Date: Oct. 17, 2019

(65) Prior Publication Data
US 2021/0095332 A1    Apr. 1, 2021

Related U.S. Application Data

(60) Provisional application No. 62/732,452, filed on Sep. 17, 2018, provisional application No. 62/657,639, filed on Apr. 13, 2018.

(51) Int. Cl.
*C12Q 1/6832*     (2018.01)

(52) U.S. Cl.
CPC ................. *C12Q 1/6832* (2013.01)

(58) Field of Classification Search
CPC ........ C12Q 2525/161; C12Q 2527/143; C12Q 1/6813
See application file for complete search history.

(56) References Cited

U.S. PATENT DOCUMENTS

2018/0057864 A1*   3/2018   Jacky .................. C12Q 1/6888

FOREIGN PATENT DOCUMENTS

WO    WO 2017/079593 A1    5/2017
WO    WO-2017079593 A1 *   5/2017 ......... C12N 15/1096
WO    WO-2017173035 A1 *   10/2017 ......... C12Q 1/6804

* cited by examiner

*Primary Examiner* — Young J Kim
(74) *Attorney, Agent, or Firm* — James S. Keddie; Bozicevic, Field & Francis LLP

(57) ABSTRACT

This disclosure provides, among other things, a reagent system for nucleic acid analysis. In some embodiments, the system may comprise a plurality of oligonucleotide sets each set comprising at least (a) a competitor oligonucleotide that hybridizes to a target sequence and varies in concentration from mixture to mixture and (b) a detector oligonucleotide that also hybridizes to the target sequence and contains a barcode that indicates the concentration of the competitor oligonucleotide in the oligonucleotide set. The reagent system may be used to analyze a nucleic acid sample.

20 Claims, 21 Drawing Sheets

Current quantitation by Seq is inefficient. It works by counting:

Much more efficient would be a *positional (decimal) representation*:

GAPDH    2712 hTERT    3

Counting requires 2712+3 = 2715 reads to report these abundances. By contrast, if each decimal position can be conveyed with ~10 reads then the positional representation requires only 5×10 = 50 reads, exponentially less than counting.

EXTENSION PROBES:

*target / target code*    *detector probe*    *competitor*

 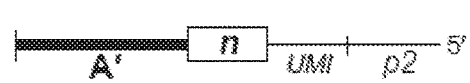 

p1, p2 = PCR handles    n = code indicating round    kill = extension on this
UMI = unique molecular identifier    destroys ability to extend
(optional)    on detector probes.

HYBRIDIZATION

*with detector*    *with competitor*

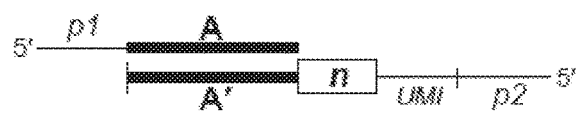 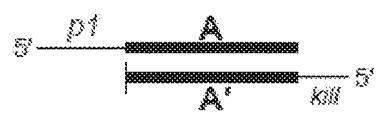

POLYMERASE EXTENSION

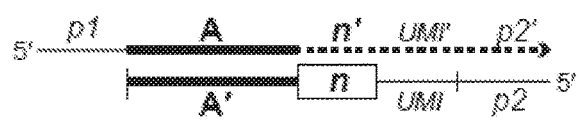 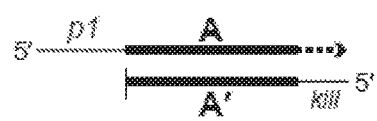

extension product on a detector probe can be amplified by PCR (with primers p1 and p2)

extension product on the competitor is a dead-end.

FIG. 3

HYBRIDIZATION PROBES:
*detector probe*  *competitor* 
n = code indicating round
UMI = unique molecular identifier (optional)
p1, p2 = PCR handles
*HYBRIDIZATION*
(targets immobilized on solid-phase, either before or after hybridization)
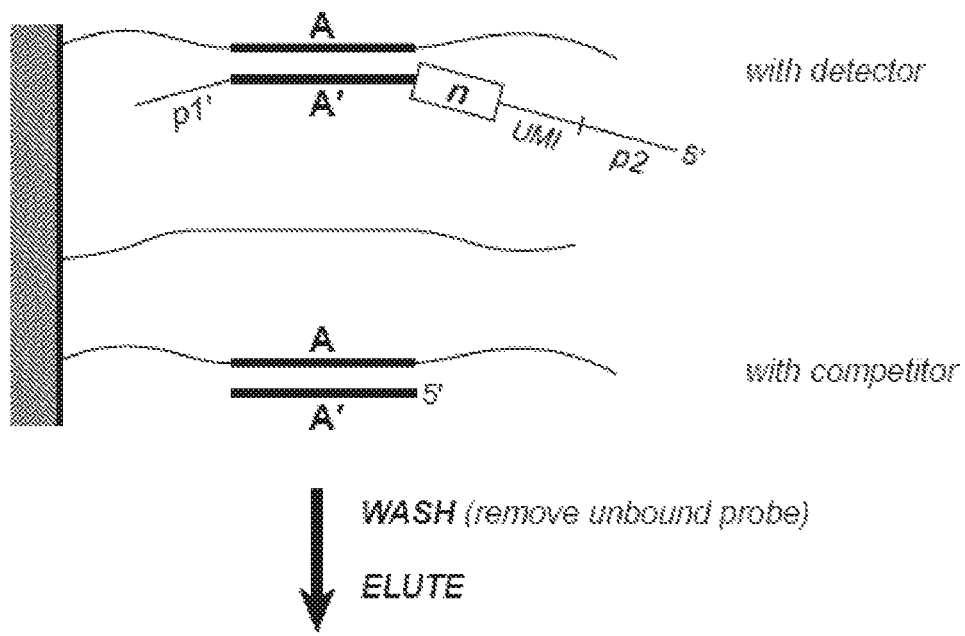
only detector probes can be PCR-amplified
FIG. 4

LIGATION PROBES:

*detector hemi-probes*            *competitor*

 

$n$ = code indicating round
$UMI$ = unique molecular identifier (optional)
P = 5'-phosphate
p1, p2 = PCR handles

HYBRIDIZATION
(preferably, targets immobilized on solid-phase)
p1' hemi-probes are in excess.

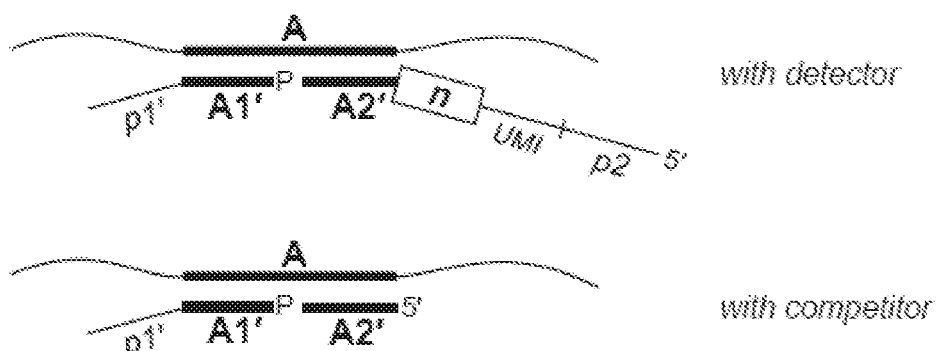

*with detector*

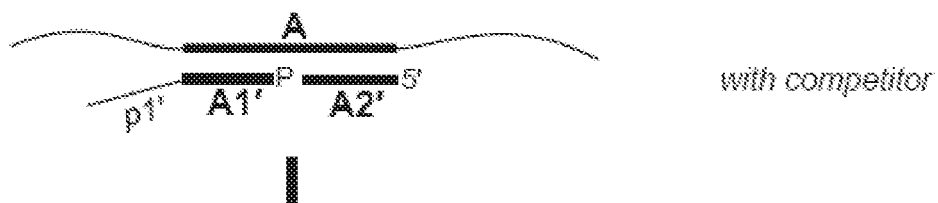

*with competitor*

LIGATION

only ligated detector probes can be PCR-amplified

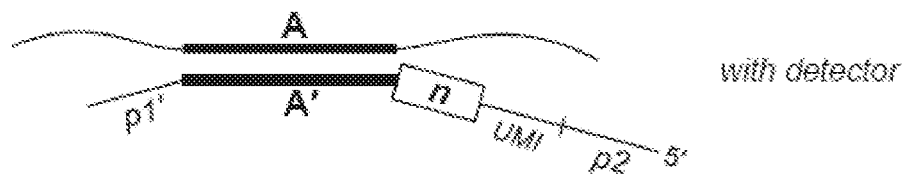

*with detector*

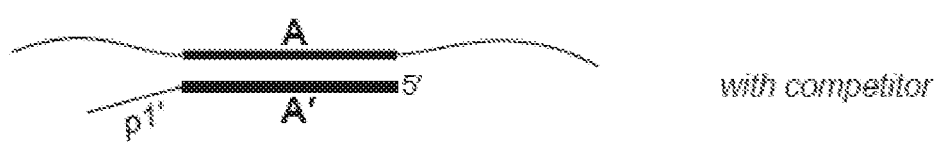

*with competitor*

FIG. 5

PADLOCK PROBES / MOLECULAR INVERSION PROBES (M.I.P.):

*detector probes*                                  *competitor*

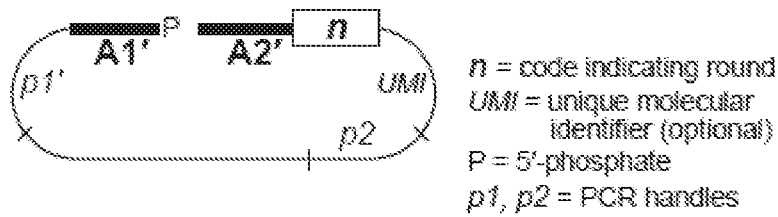 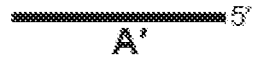

n = code indicating round
UMI = unique molecular identifier (optional)
P = 5'-phosphate
p1, p2 = PCR handles

HYBRIDIZATION

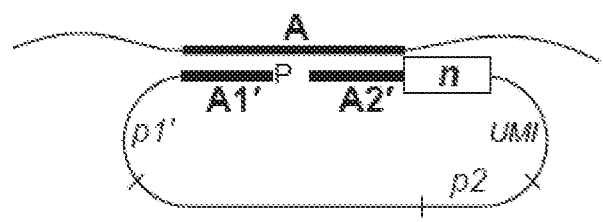

*with detector*

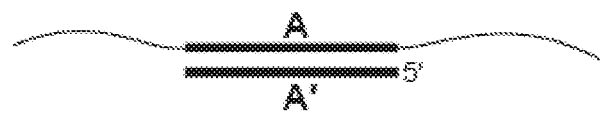

*with competitor*

LIGATION
*If M.I.P., ALSO GAP-FILL WITH POLYMERASE*

unligated probes can be destroyed by exonuclease;
only ligated detector probes can be PCR-amplified

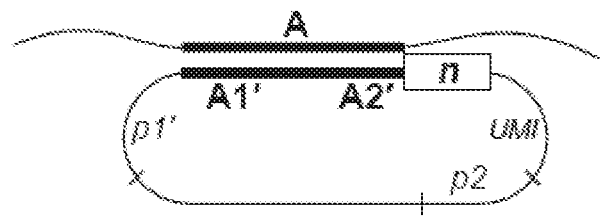

*with detector*

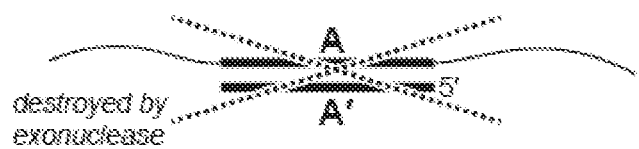

*with competitor* destroyed by exonuclease

FIG. 6

GENERAL SCHEME FOR INDIRECT (MODULAR) DETECTION USING TARGET-CODES:

*target-code probes*

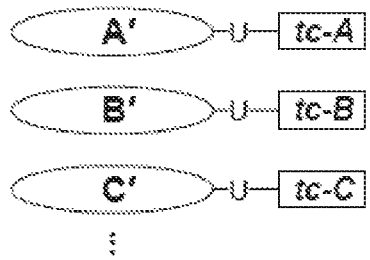

X' = recognition reagent for target X
(could be nucleic acid, protein, small molecule)
U = cleavable joint (e.g., deoxyuracil)
tc-X = DNA code for target X

INTERACTION WITH TARGETS
*Probes interact with targets in proportion to their abundances.*

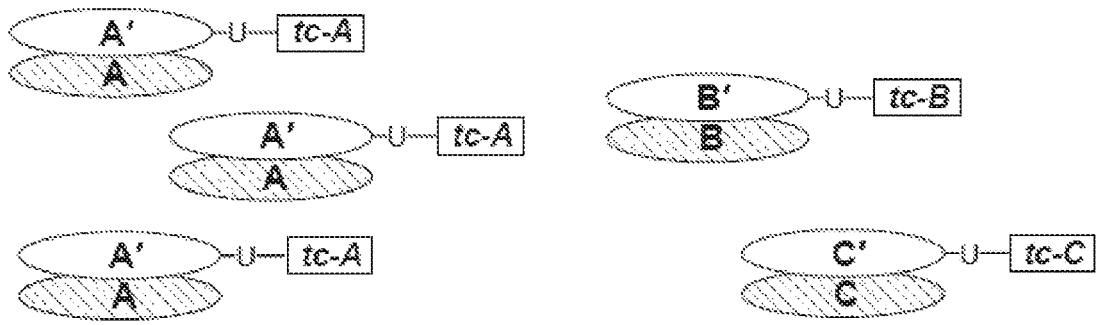

REMOVE EXCESS PROBES
(e.g. by washing)

CLEAVE TARGET-CODES
(e.g., with uracil glycosylase)

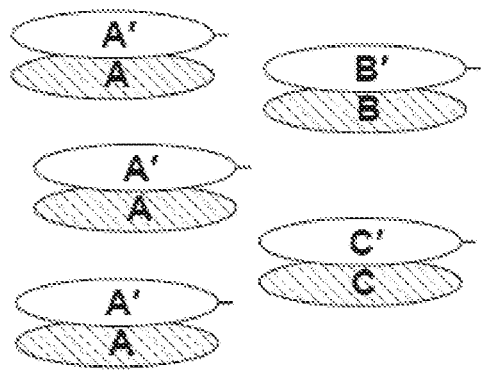

*released target-codes have abundances proportional to the original targets. they can be meaured by preceding methods.*

— tc-A
— tc-A
— tc-A
— tc-B
— tc-C the set of target-codes and reagents for their scaled quantitation are modular: via different target-code probes, they can be used to measure many different types of input.

FIG. 7

HYBRIDIZATION PROBES WITH TARGET-CODES, FOR INDIRECT (MODULAR) DETECTION:

*target-code probes*

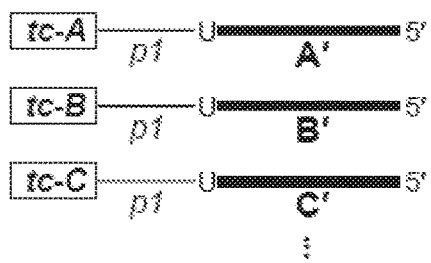

*target-code portion here designed to work with extension probes after release.*

*tc-X* = code for target X
*p1* = PCR handle
U = cleavable joint (e.g., deoxyuracil)

HYBRIDIZATION
*(targets immobilized on solid-phase, either before or after hybridization)*
*Probes interact with targets in proportion to their abundances.*

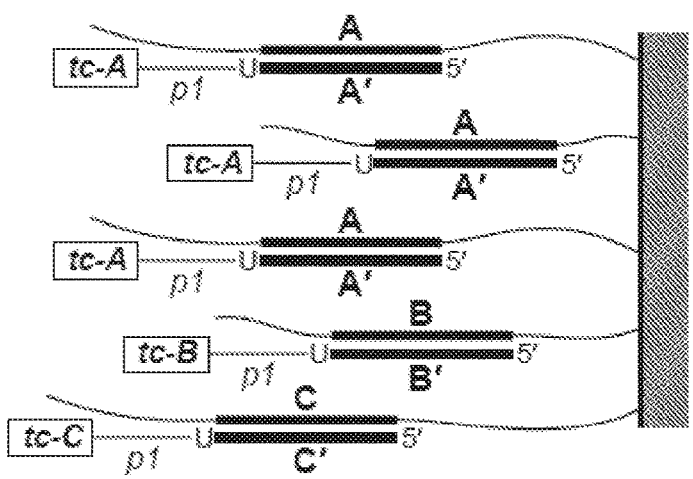

WASH
*(remove unbound probes)*

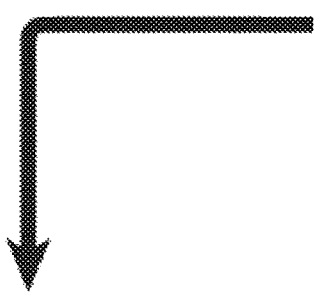

CLEAVE TARGET-CODES
*(e.g., with uracil glycosylase)*

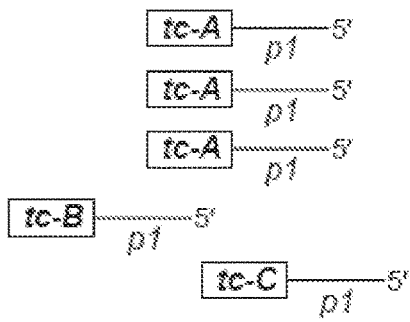

released target-codes are ready for next module, e.g. quantitation by extension probes.

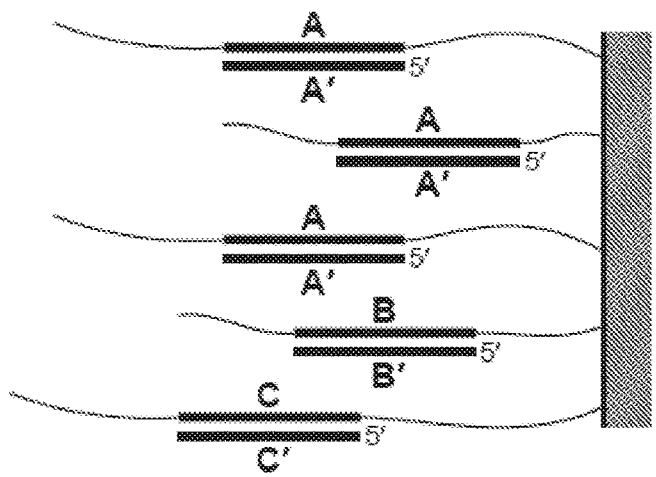

FIG. 8

ANTIBODY PROBES WITH TARGET-CODES, FOR INDIRECT (MODULAR) DETECTION

*target-code probes = target-specific antibodies labeled with oligos*

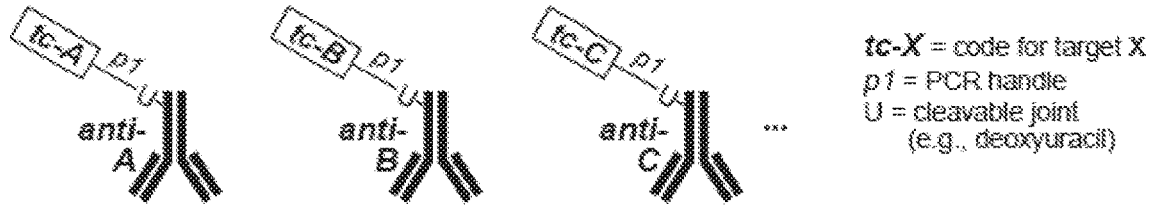

tc-X = code for target X
p1 = PCR handle
U = cleavable joint
 (e.g., deoxyuracil)

BINDING
solid-phase targets (tissue sections, wells, beads, microarrays) or solution targets possible using methods like proximity ligation. Antibodies interact with targets in proportion to their abundances.

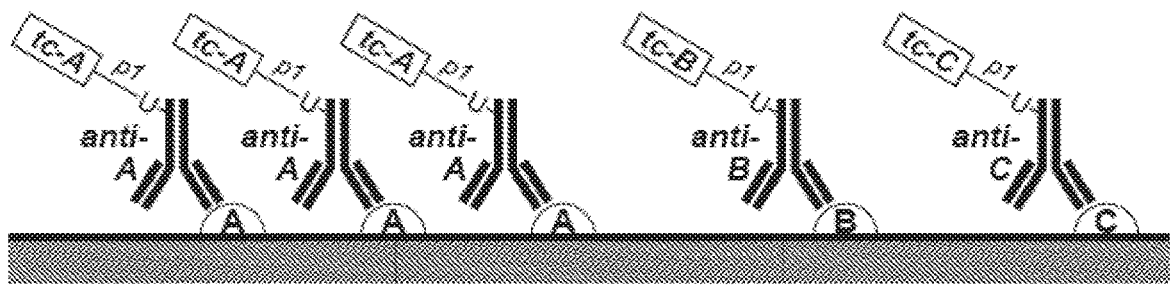

WASH
(remove unbound antibodies)

ELUTE BY CLEAVAGE
(e.g., uracil glycosylase)

released target-codes are ready for next module, e.g. quantitation with extension probes.

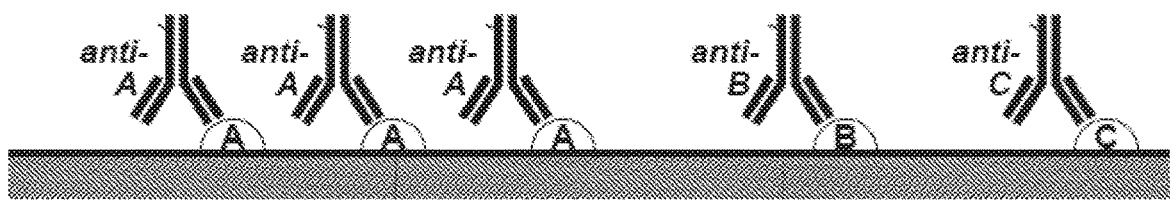

FIG. 9

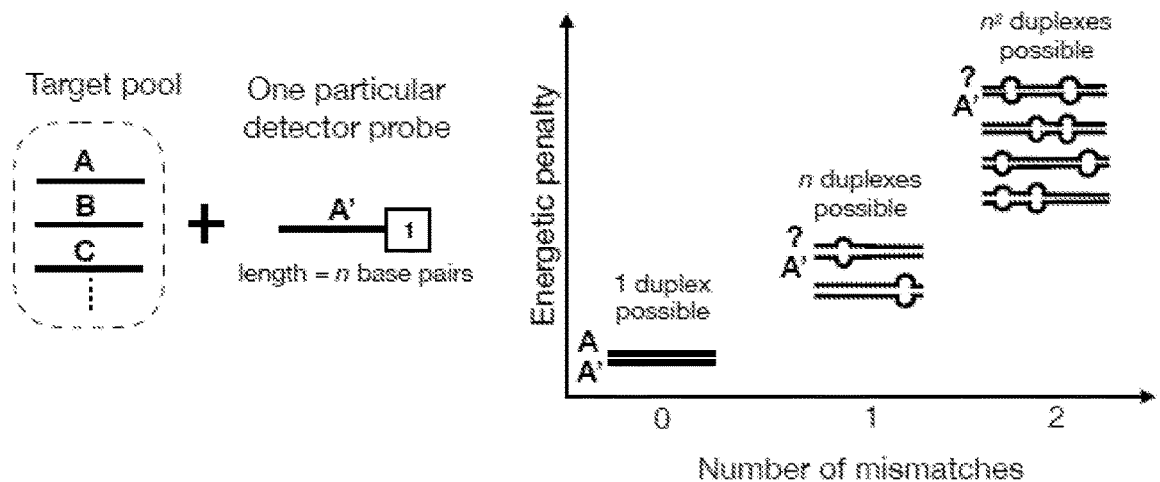
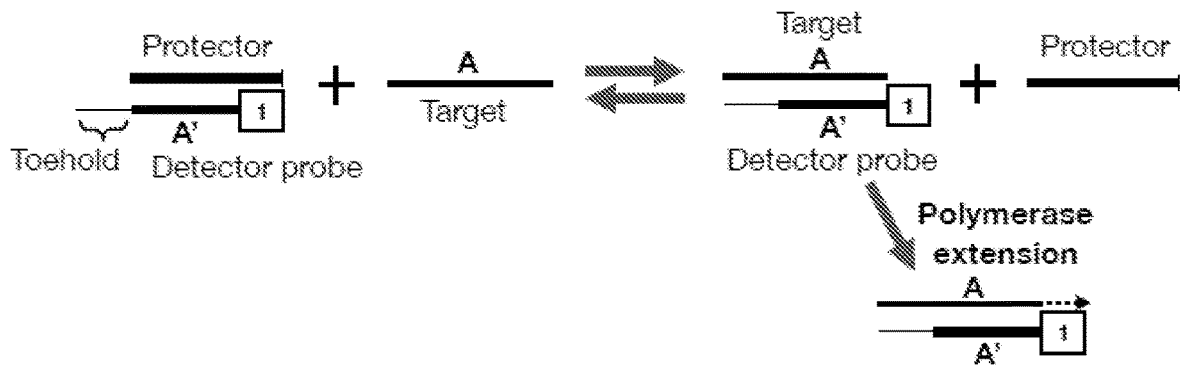
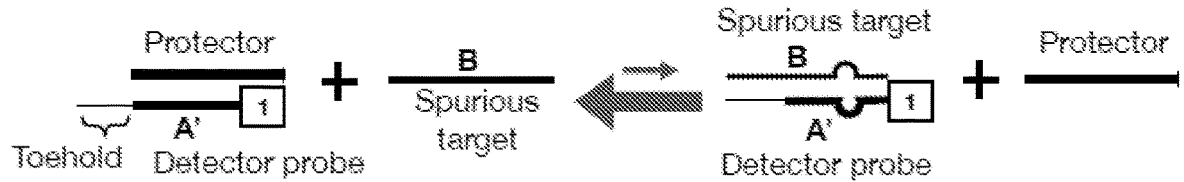
FIG. 11

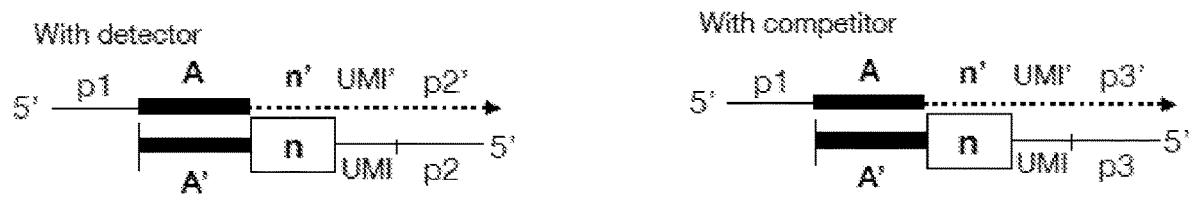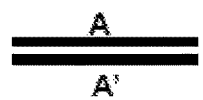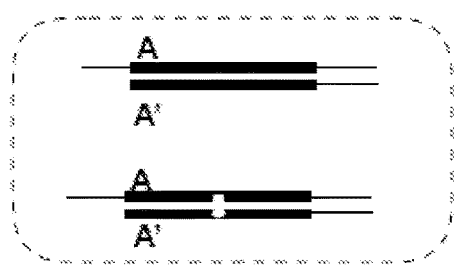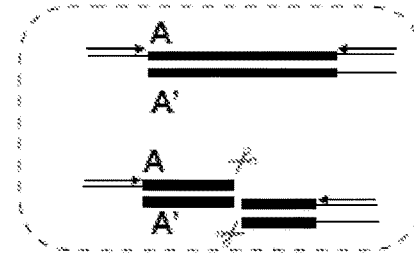
FIG. 16 a.

| Code1 | Code2 | Code3 | Code4 | Code5 | Code6 | Ground Truth | SEM |
|---|---|---|---|---|---|---|---|
| 165 | 344 | 310 | 148 | 10 | 0 | 79954 | 277211 |
| 39 | 82 | 95 | 43 | 8 | 2 | 79954 | 160782 |
| 49 | 88 | 54 | 37 | 2 | 0 | 7996 | 65349 |
| 7 | 13 | 8 | 9 | 1 | 0 | 800 | 19974 |
| 0 | 9 | 13 | 2 | 0 | 0 | 800 | 5507 |
| 0 | 4 | 2 | 1 | 0 | 0 | 1 | 1765 |
| 0 | 1 | 1 | 1 | 0 | 0 | 1 | 1545 |
| 1 | 1 | 3 | 0 | 0 | 0 | 80 | 701 |
| 0 | 2 | 2 | 0 | 0 | 0 | 1 | 512 | b.

| Code Sum | Ground Truth |
|---|---|
| 5128 | 79955 |
| 1399 | 79955 |
| 1000 | 7996 |
| 337 | 800.5 |
| 115 | 1 |
| 109 | 1 |
| 95 | 800.5 |
| 59 | 1 |
| 54 | 1 |
| 47 | 1 |
| 28 | 80.95 |
| 28 | 1 |
| 26 | 1 |

NUCLEIC ACID QUANTIFICATION USING CONCENTRATION-SPECIFIC BARCODES

CROSS-REFERENCING

This application is a § 371 national phase of International Application No. PCT/US2019/027365, filed on Apr. 12, 2019, which claims the benefit of U.S. provisional application Ser. No. 62/657,639, filed Apr. 13, 2018, and 62/732,452, filed Sep. 17, 2018, which applications are incorporated by reference herein.

GOVERNMENT RIGHTS

This invention was made with Government support under contract 1552196 awarded by the National Science Foundation and under contract GM116847 awarded by the National Institutes of Health. The Government has certain rights in the invention.

BACKGROUND

In many nucleic acid samples, there may be several orders of magnitude difference between the most abundant species and the least. This makes it challenging, or at least inefficient, to quantify highly abundant and the least abundant species from the same sample using the same assay. Specifically, measurement of molecular abundance is fundamental to basic science and to medicine; it is a classical statistical problem formalized as the problem of estimating the multiplicities $n_i$ of elements $s_i$ in a so-called multiset, and traditionally solved with simple random sampling (SRS). Next-generation sequencing enables SRS of molecules to be performed at high throughput, but in many applications, current or projected throughput is insufficient for addressing critical problems in medicine (e.g. next-generation biomarker detection), chemistry (e.g. high throughput compound screens) and biology (e.g. single-cell sequencing); it is insufficient because SRS suffers from intrinsic limitations when: (i) the cardinality of the multiset is comparable or large compared to the number of measurements taken; (ii) large discrepancies exist between the $n_i$; (iii) or when precise detection of small changes between the $n_i$ is required. A variety of molecular technologies have attempted to address inefficiencies, including targeted or semi-unbiased enrichment or depletion of a population of molecules (Boone, De Koker, Callewaert, 2018; Hubank & Schatz, 1994). However, these technologies are only semi-quantitative as they compromise quantification of a set of sequences subject to the depletion and require the depleted or enriched sequences to be prespecified.

SUMMARY

This disclosure provides, among other things, a method of sample analysis. In some embodiments the method may comprise: (a) obtaining a reagent system comprising: a plurality of oligonucleotide sets, each set comprising: i. a first detector oligonucleotide comprising a sequence that is complementary to a target sequence and a barcode that is 5' of the target-complementary sequence; and ii. a first competitor oligonucleotide that does not comprise the barcode and competes with the first detector oligonucleotide for binding to the target sequence; wherein: i. the concentration of the competitor oligonucleotide is different in each of the oligonucleotide sets; and ii. the barcode sequence is different in each oligonucleotide set and indicates the concentration of the first competitor oligonucleotide in the oligonucleotide set; (b) sequentially hybridizing the oligonucleotide sets of (a) with a sample that comprises a population of molecules that comprise the target sequence, wherein the oligonucleotide sets are hybridized in order of increasing concentration of the competitor oligonucleotide; and (c) quantifying the amount of each barcode in the detector oligonucleotides that hybridize to the population of molecules in step (b).

The quantifying step may be done in a variety of different ways. In some embodiments, the quantifying step may comprises performing a biochemical reaction on the hybridization products after hybridization of each of the oligonucleotide set and analyzing the reaction products. For example, in some embodiments, the biochemical reaction may comprise: i. extending the hybridized target sequence using the detector oligonucleotides as a template, thereby producing primer extension products that comprise the complement of the barcodes of the hybridized detector oligonucleotides or ii. extending the hybridized detector oligonucleotides using the target sequence as a template, thereby producing primer extension products that comprise the barcodes of the hybridized detector oligonucleotides. In these embodiments, the method may comprise quantifying the amount of each barcode, or complement thereof, in the primer extension products.

As will be explained in greater detail below, the oligonucleotide set may be in a separate containers, or mixed together in the same container A reagent mix for performing the method is also provided.

The method finds in a variety of sample analysis methods. In particular, the method finds use in molecular screens and for detecting proteins. In these embodiments, the target sequence may be a sequence in a library of guide RNAs, a phage display library, oligonucleotide-tagged combinatorial chemistry library or the like, for example, or a sequence in oligonucleotides that have been cleaved from a binding agent such as an antibody.

BRIEF DESCRIPTION OF THE FIGURES

The skilled artisan will understand that the drawings, described below, are for illustration purposes only. The drawings are not intended to limit the scope of the present teachings in any way.

FIG. 3 shows how probe interaction with sequence targets can be made selectable using polymerase extension ("Extension Probes"). In this method, it is assumed that the target pool has been engineered to already contain one PCR handle (sequence suitable for priming of PCR). This may be added (e.g., by ligation) or be present as part of target design (especially in the case of indirect/modular analysis, see FIGS. 8 and 9, where the target sequence subjected herein is in fact an arbitrary code representing another, original, target sequence; that is, it is a "target-code").

Figure 1:
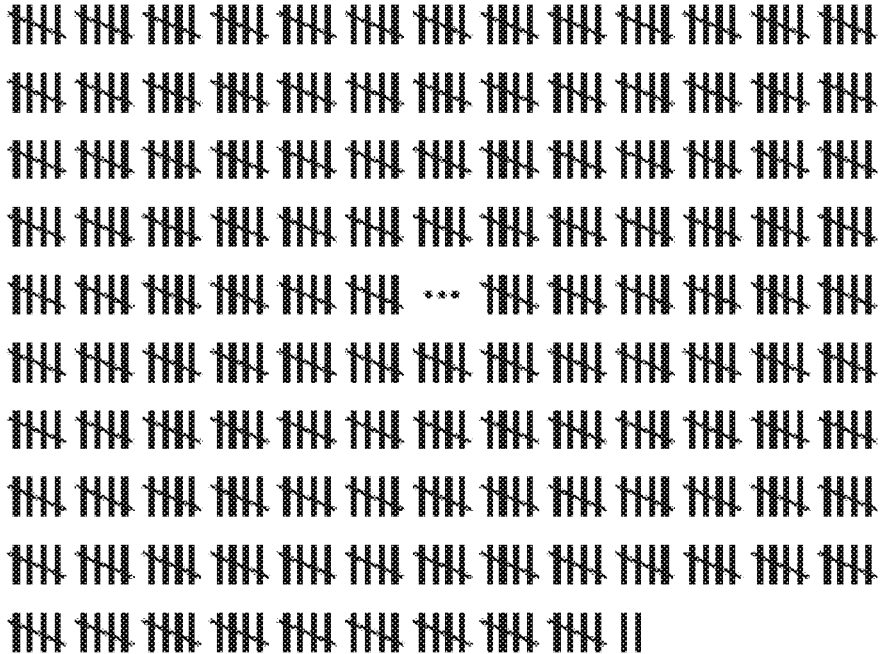
FIG. 1 shows a comparison between the amounts of effort required to analyze the abundance of two sequences (GAPDH and hTERT) using conventional sequencing (top) and an embodiment of the present method (bottom). In addition to the greater economy of a positional representation, the present method can have greater accuracy for less abundant species than counting. In a positional scheme, one can increase accuracy for hTERT dramatically simply by increasing the number of observations for each position (say 50 observations per round, rather than 10).

The probes contain a region complementary to the target. When the target and probe hybridize, the target strand can be extended by polymerase to copy the round-code (represented as boxed "n") and the second PCR handle. Only after such an extension reaction is the target strand capable of being amplified by PCR. Additional information can be incorporated as desired such as, for example, unique molecular identifiers (UMI; random sequences distinct between each molecule of probe) that can improve quantitation by accounting for PCR bias.

The competitors contain the same region complementary to the target, but do not contain the second PCR handle; interaction of competitor with target removes that target molecule from the possibility of interaction with probe, and no PCR-amplifiable product can result. Additionally, the competitor may contain a "kill" sequence, such that once a target strand has been extended on "kill", it becomes irreversibly incompatible by extension on a probe. In one instantiation, the extendable sequence of probes is designed to lack a specific base (such as G), the "kill" sequence contains this base, and the dNTP mix contains dideoxy-CTP (ddC), so that extension on "kill" (but not probes) incorporates ddC and no further extension is possible.

To limit extension to only the desired locations, the probe and competitor may be blocked at the 3' end (indicated in the figure by a vertical bar at that end).

FIG. 4 shows how probe interaction with sequence targets can be made selectable by hybridization alone ("Hybridization Probes"). Here it is assumed that the target pool can be captured onto a solid-phase; for example, by polymerase extension using primers anchored to a solid-phase, or primers with a handle, e.g., biotin, that can be captured on, e.g., streptavidin/solid-phase; or RNA may be captured by hybridization to oligo(dT)/solid-phase; or RNA/DNA can be chemically crosslinked to a solid-phase.

The probes contain a region complementary to the target as well as both handles necessary for PCR and the round-code (represented as boxed "n"). Additional information such as a UMI can also be included. Competitors contain only the target-complementary region. Hybridization of a target to either probe or competitor blocks it from further interaction. At the end of all rounds of hybridization, the unbound probes and competitors are washed away. The bound probes and competitors are eluted (e.g., with temperature or pH change). The probes can be selected by PCR amplification.

FIG. 5 shows how probe interaction with sequence targets can be made selectable by hybridization and ligation ("Ligation Probes"). It is not necessary for the target pool to be captured on a solid-phase (as in FIG. 4), however it may be preferable as it allows an additional selection factor (washing) and may simplify manipulations. The probes are in two pieces ("hemi-probes"), each being complementary to adjacent regions on the target. Each hemi-probe contains only one of the handles necessary for PCR. The downstream (3'-most) hemi-probe has a 5'-phosphate, which allows it to be ligated to; this hemi-probe will be used in excess. The upstream (5' most) hemi-probe will be used in stoichiometric amounts and contains the round-code and possibly additional information like a UMI; it can be regarded as the "probe" of the generalized scheme. This provides a level of specificity beyond simply hybridization, in that both hemi-probes must properly hybridize directly adjacent to each other on the target in order for ligation to occur; ligation is necessary for selectability of the probe (only the ligated probe has both handles needed for PCR amplification).

The competitor contains only the region complementary to the target, such that it can block the hybridization of the upstream hemi-probe. As pictured here, the competitor is capable of being ligated to the downstream hemi-probe, but that ligation product cannot be amplified since it has only one of the PCR handles. It is also possible to design competitors so they are blocked at the 3' end and cannot ligate, or such that they overlap the two complementary regions of the hemi-probes (such that if competitor is hybridized, neither hemi-probe can hybridize).

FIG. 6 shows how probe interaction with sequence targets can be made selectable by circular ligation ("Padlock Probes" and "Molecular Inversion Probes (MIPs)". The probes contain segments at each end complementary to adjacent (for padlock) or nearby (for MIPs) regions on the target. Although both PCR handles are present, they are separated by a break. The probes also contain the round-code and possibly additional information like a UMI. This provides a level of specificity beyond simply hybridization, in that both segments of the probe must properly hybridize directly adjacent (for padlock) on the target in order for ligation to occur. For MIPs, the targeting segments are not adjacent and so also require fill-in of the gap by a polymerase before ligation can occur. Ligation is necessary for selectability of the probe (only the ligated probe has the two PCR handles properly connected to allow PCR amplification). The competitor contains only the region complementary to the target, such that it can block the hybridization of detector probe.

FIG. 7 shows the generalized scheme that allows an embodiment of the present method to be used in a modular way, and thus applied to the measurement of diverse entities, in particular not limited to measurement of nucleic acids.

This method uses a collection of reagents that can recognize specific target molecules and that are tagged with oligonucleotides. In the preceding figures, the recognition reagents were complementary nucleic acids. However, they could also be nucleic acid aptamers, proteins such as antibodies, or small molecules. The oligonucleotide tags are designed to associate a particular sequence code with each target-specific reagent (a "target-code"), to have a cleavable linkage (such as deoxyuracil), and whatever additional properties are required so that when they are released from the recognition reagent they can be measured by one of the scaled quantitation methods described previously herein.

The tagged reagents, "target-code probes", are incubated with their target molecules under circumstances where the bound probes can be separated from excess unbound probes. Most commonly this will be because the bound probes become immobilized on a solid-phase and unbound probes can be washed away; but other schemes are possible (for example, proximity ligation).

Then the linkage is cleaved and the released target-codes are collected. This creates a population of target-codes that mirrors the abundances of the original targets. Thus, the scaled quantitation of the target-codes directly reflects the abundances of the original targets.

The indirection or modularity provided by this approach is advantageous because scaled quantitation for a large variety of inputs can be done with a single universal set or reagents, rather than requiring a custom set of reagents for each application. It also makes it possible to use these approaches for measurement of targets that are not nucleic acids, for example, proteins.

The method shown in FIG. 7 may be readily adapted to work any of the detection methods shown in FIGS. 3-6.

FIG. 8 shows how the indirect or modular scheme outlined in FIG. 7 can be applied to measuring sequences, for example, cDNAs immobilized on a solid-phase. In particular, here the target-codes are designed to be measured using the extension probe approach of FIG. 3 (but other schemes could be used). The "recognition reagent" in this case is a DNA sequence complementary to the target cDNA and can be synthesized in one piece together with the target-code; the cleavable linkage is a deoxyuracil residue. The target-code probes are hybridized in excess with the cDNA, and unbound probes are washed away. Uracil glycosylase is used to cleave off the target-codes. The released target-codes should have abundances that are proportional to the abundances of their target cDNAs, and can be measured using extension probes. The method shown in FIG. 8 may be readily adapted to work any of the detection methods shown in FIGS. 3-6.

FIG. 9 shows how the indirect or modular scheme outlined in FIG. 7 can be applied to measuring proteins or other antibody targets. As in FIG. 8, here the target-codes are designed to be measured using the extension probe approach of FIG. 3. The "recognition reagents" in this case are target-specific antibodies. The target-code oligonucleotides are covalently linked to the antibodies or possibly joined by a strong interaction such as biotin-streptavidin. It is assumed that the targets to be recognized are immobilized on a solid-phase, though other selection schemes (such as proximity ligation) are possible. The target-code probes (antibodies) are incubated in excess with the targets, and unbound probes are washed away. Uracil glycosylase is used to cleave off the target-codes. The released target-codes should have abundances that are proportional to the abundances of their target proteins, and can be measured using extension probes. The method shown in FIG. 9 may be readily adapted to work any of the detection methods shown in FIGS. 3-6.

Figure 10:
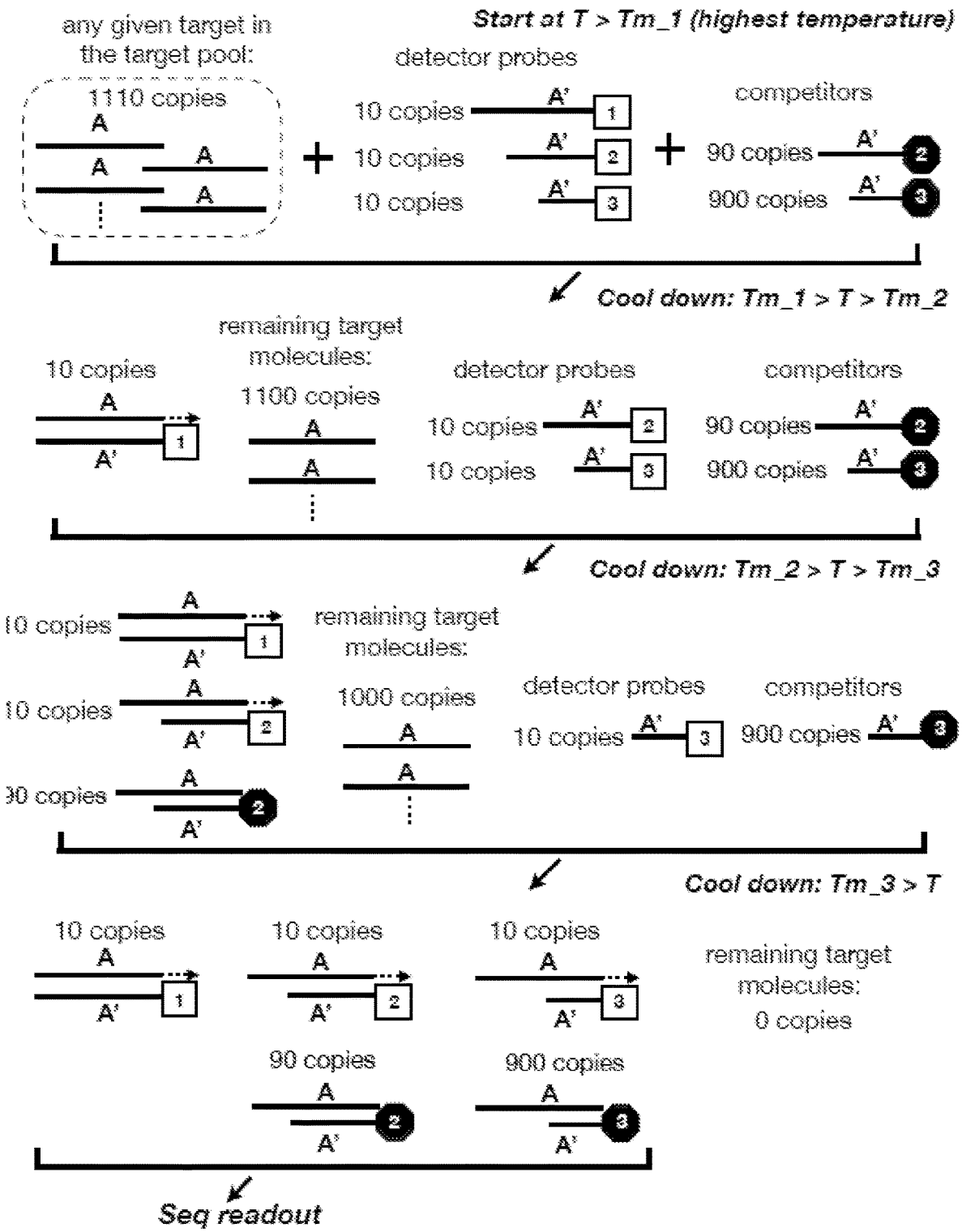

FIG. 10 illustrates how the presented method can be implemented in a single reaction without adding additional components by reducing the temperature of incubation in a stepwise manner.

FIG. 11 illustrates how the specificity of the present method can be increased using "toehold" oligonucleotides.

Figure 12:
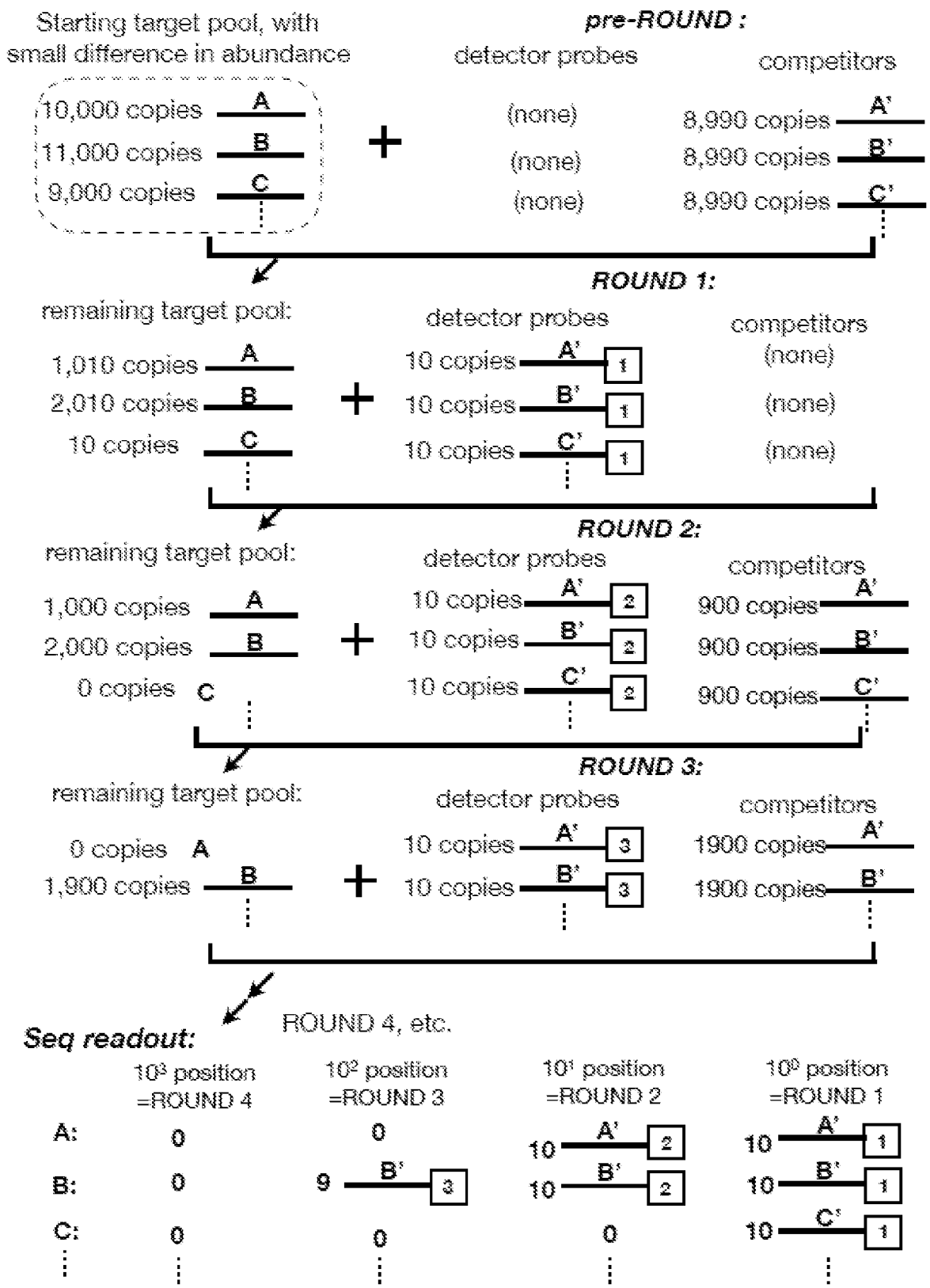

FIG. 12 illustrates how the present method can be used to quantify molecules with high resolution.

Figure 13:
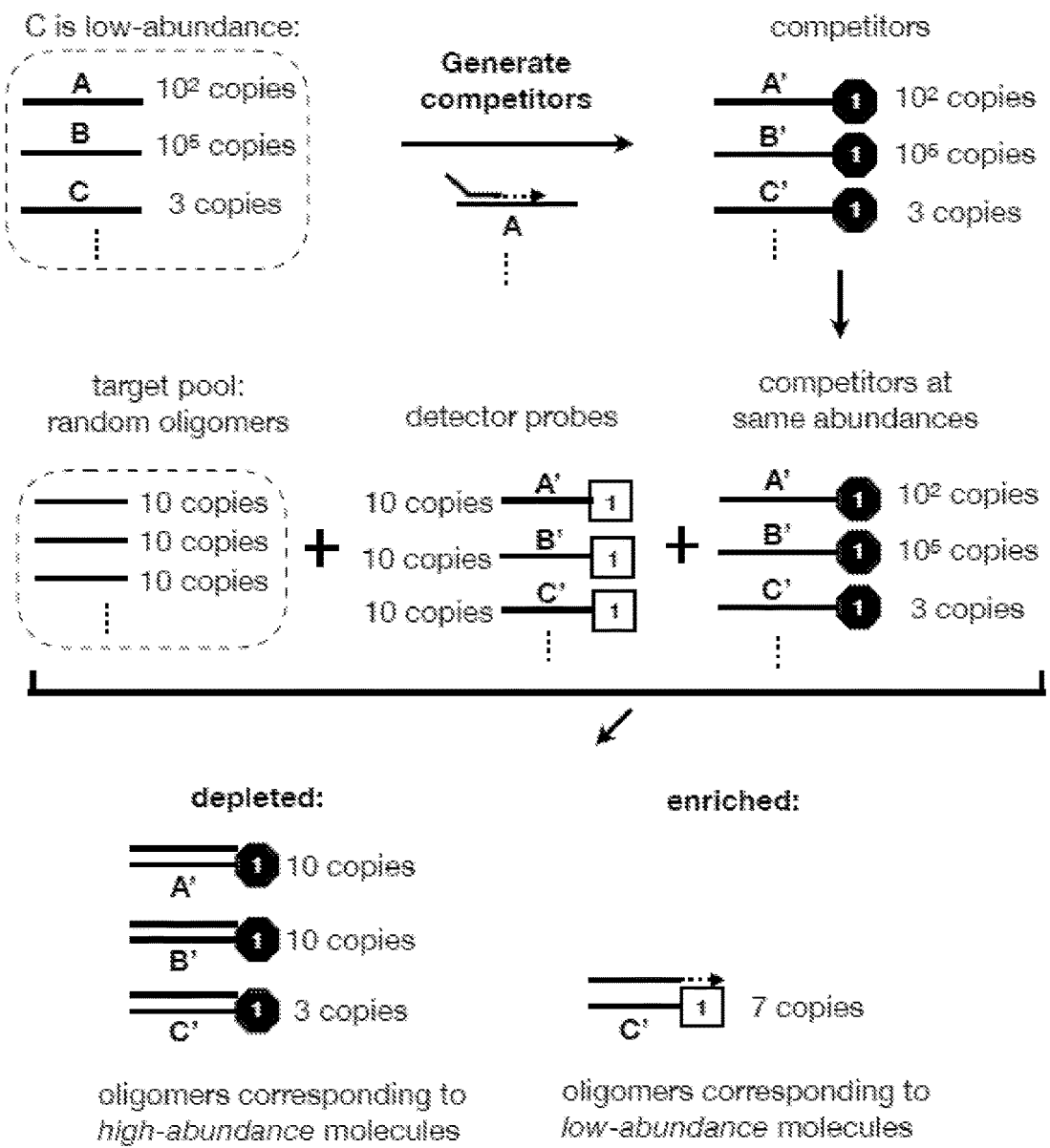

FIG. 13 illustrates how low-abundance or dropout species can be enriched.

Figure 14:
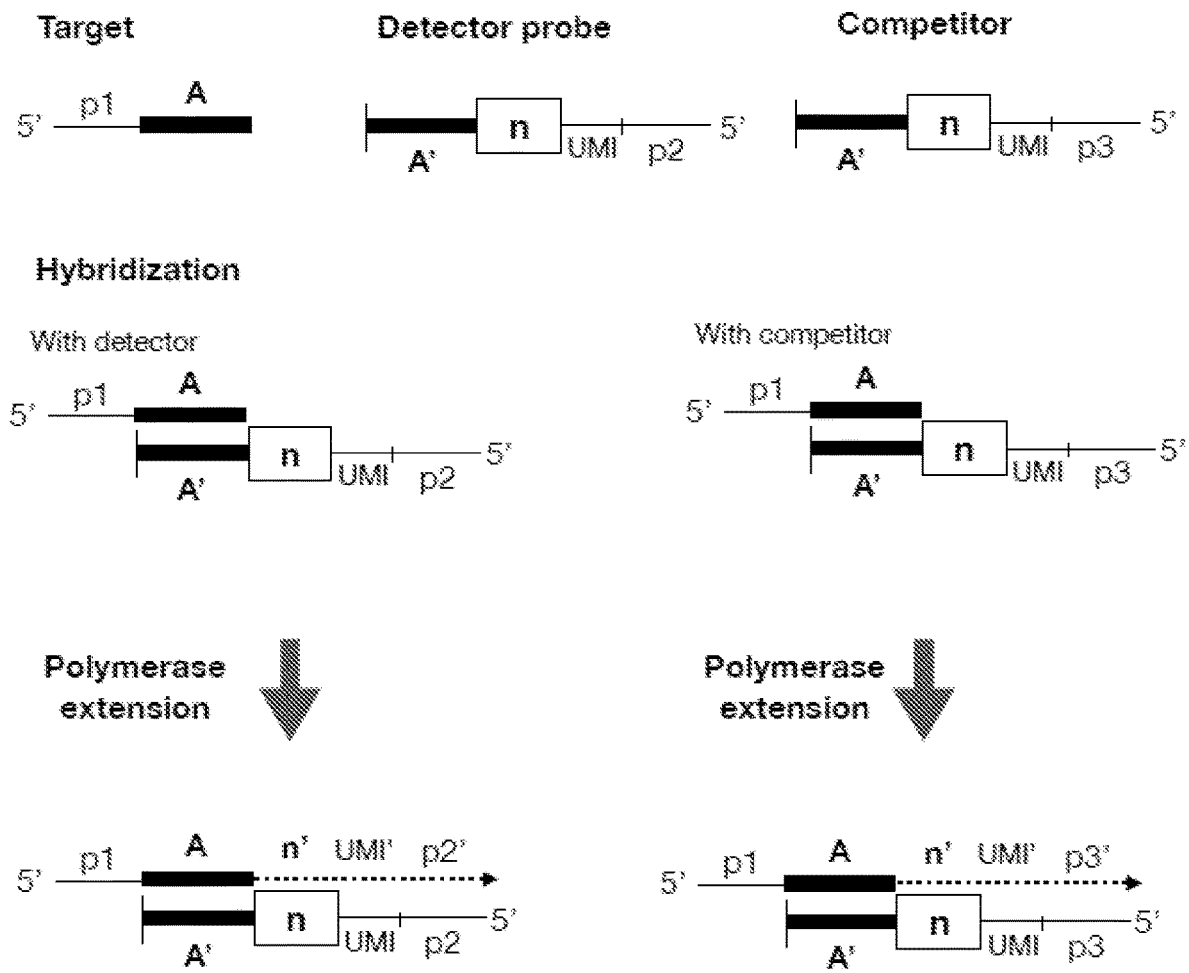

FIG. 14 illustrates a method in which the competed out molecules (i.e., those target molecules that are hybridized to a competitor oligonucleotide) can be captured and amplified, and analyzed.

Figure 15:
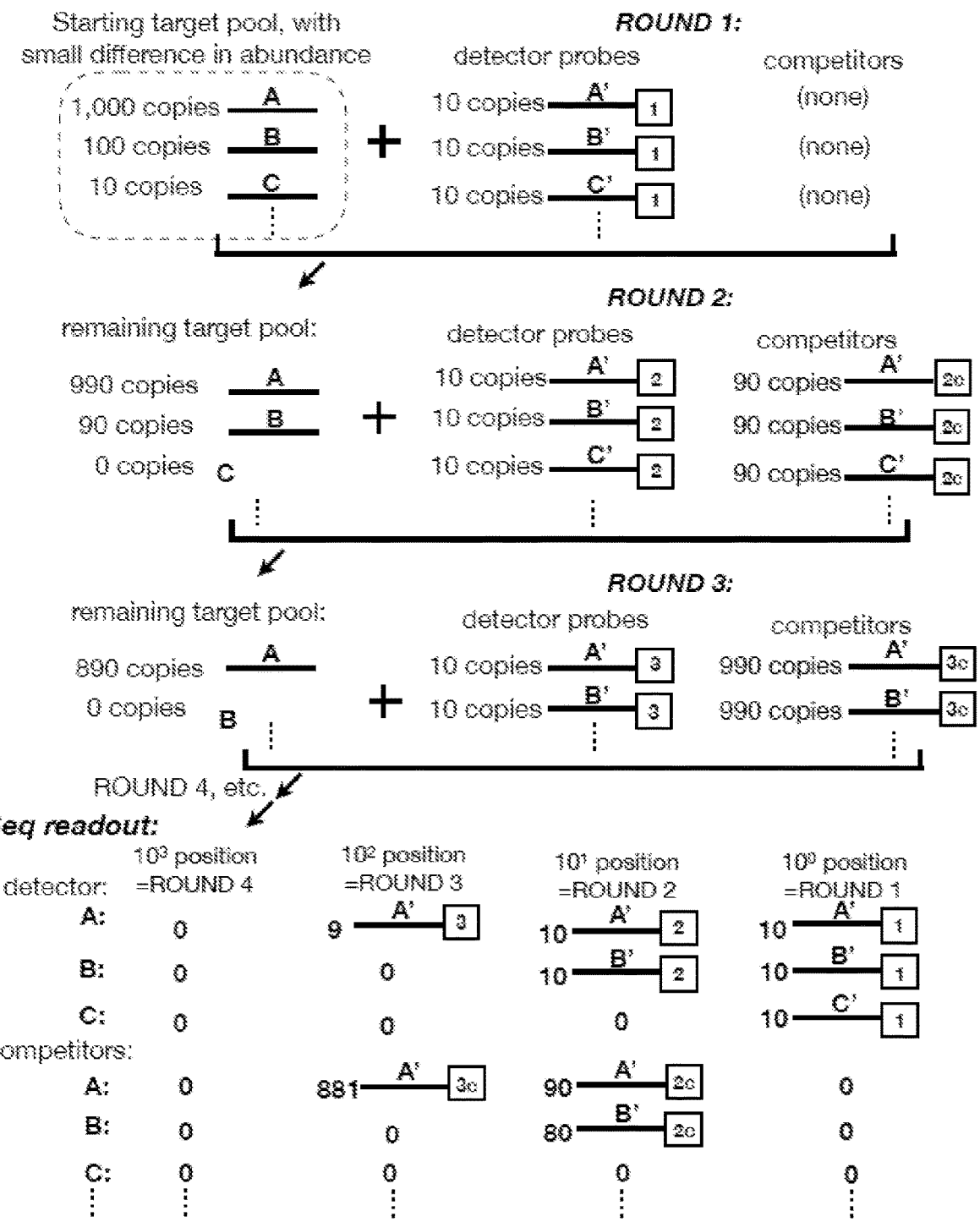

FIG. 15 illustrates how the competed out molecules (i.e., those target molecules that are hybridized to a competitor oligonucleotide) can be analyzed.

FIG. 16 illustrates how a mismatch-specific endonuclease can be used to improve detection accuracy.

Figure 17:
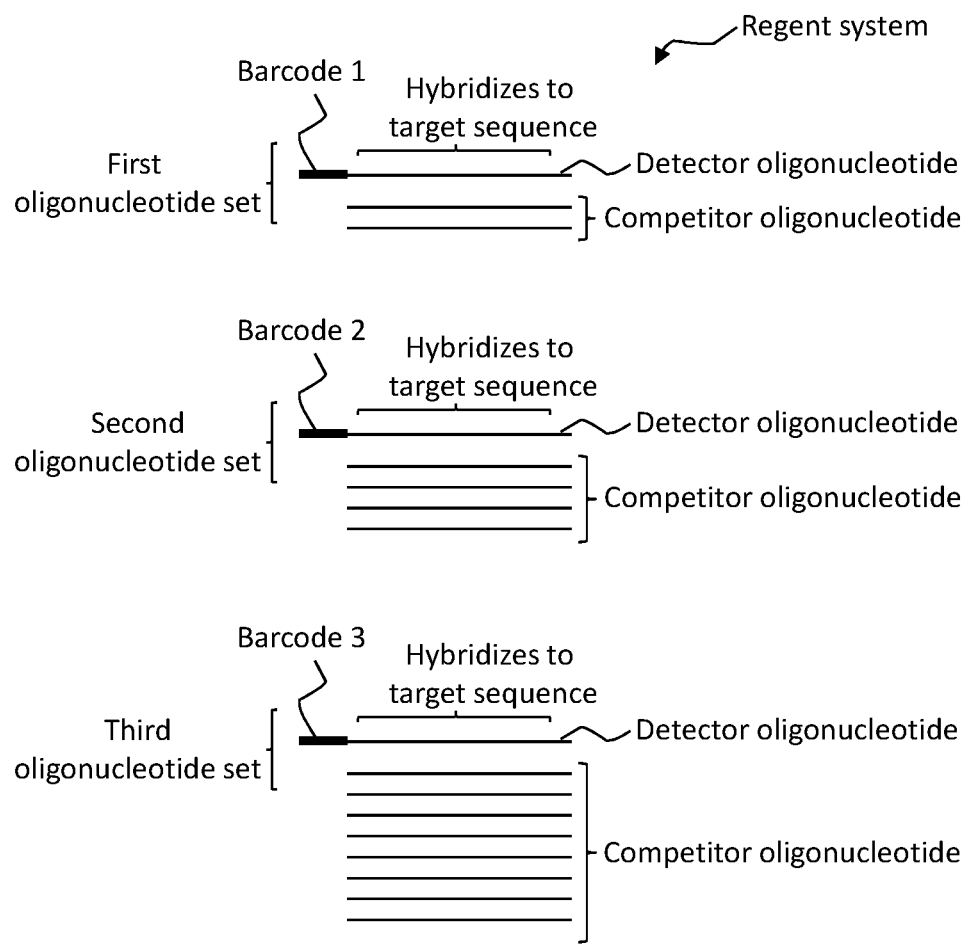

FIG. 17 schematically illustrates an exemplary reagent system.

Figure 18:
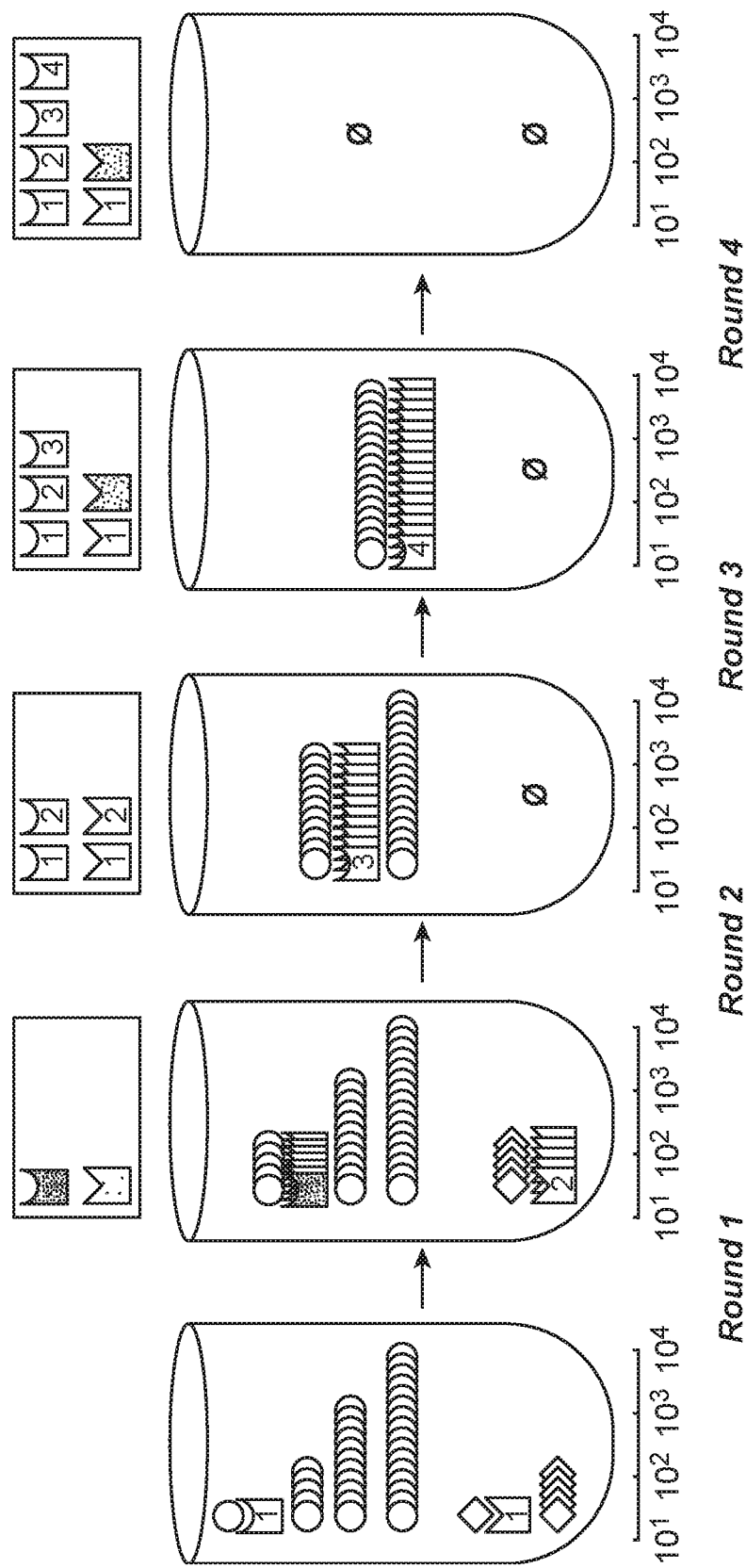

FIG. 18 provides a stylized illustration of SQUICH acting in parallel on spheres and cubes: each interact in parallel with limiting encoders and competitors. When an encoder interacts with a shape, the shape is labeled with that step at which it interacts with the encoder and is brought to a sampling box. The process continues sequentially: encoders are constant amounts while competitor abundance increases (here geometrically). If this geometric increase is in base 10, observation of a tag with the number "4" implies that the original number of molecules in the tube exceeded $10^4$. The total number of shapes in the sampling box is low, requiring very few samples to fully sample it.

Figure 19:
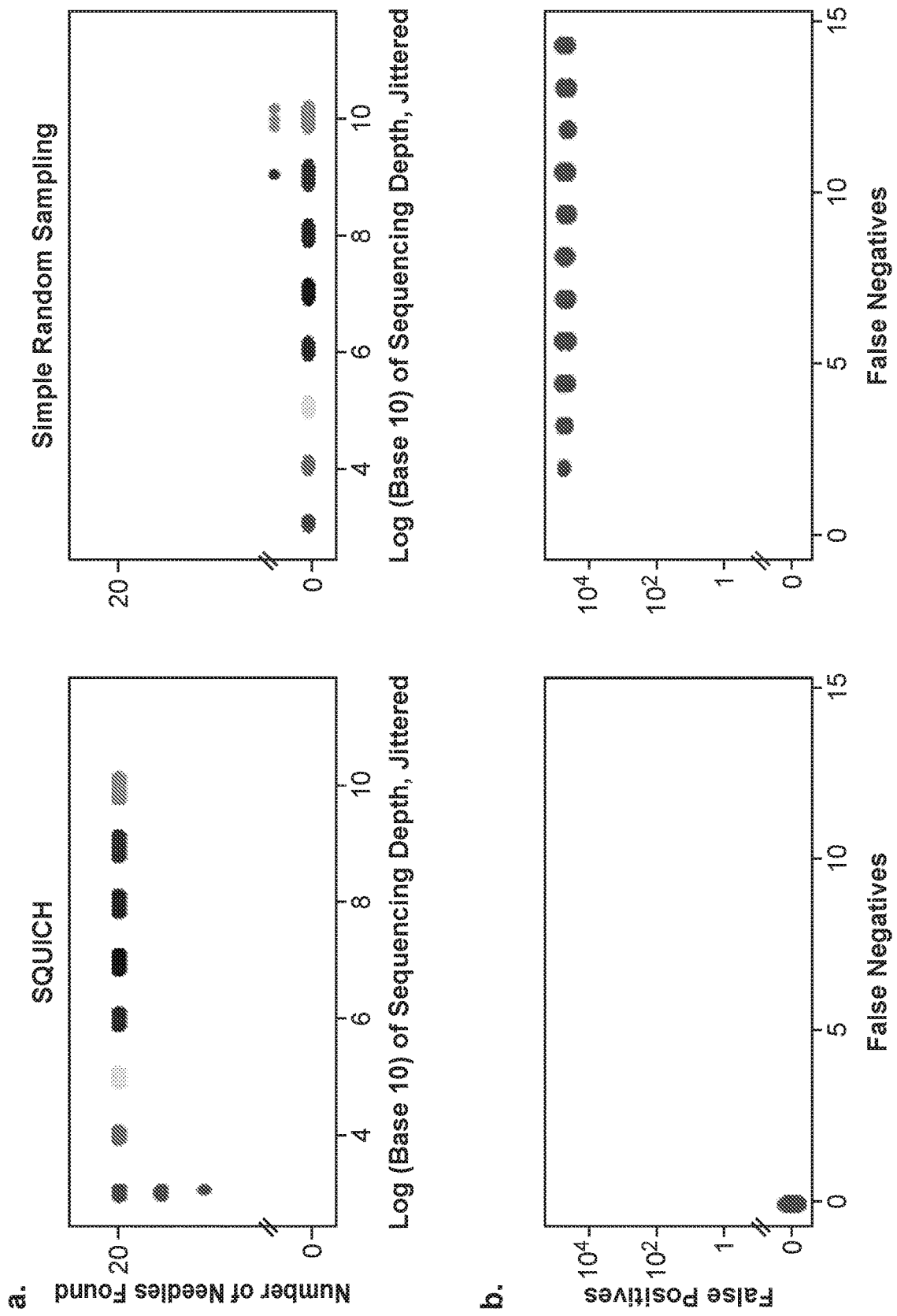
Figure 19:
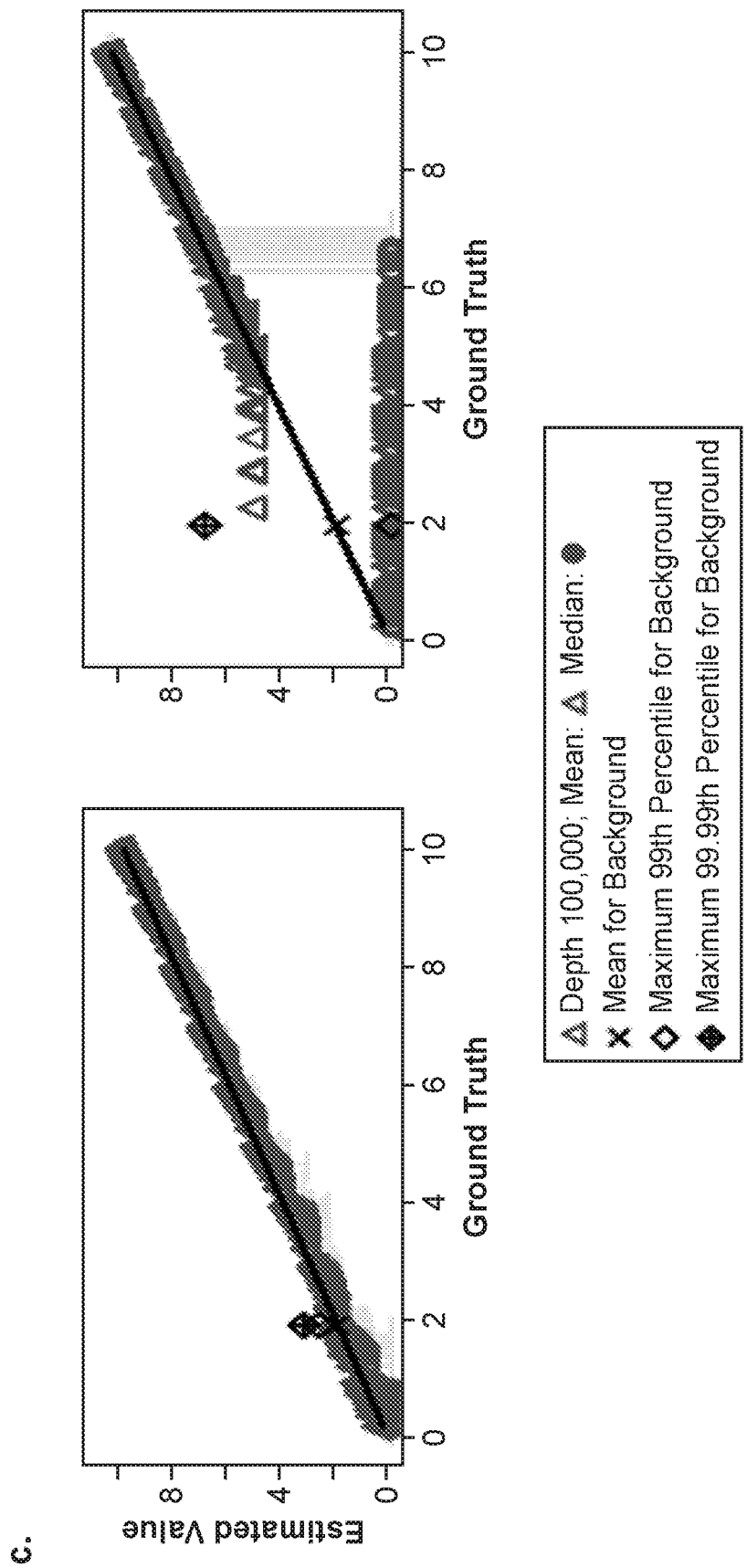

FIG. 19 provides a: In a background of two species at abundance $10^{15}$, SQUICH (L) detects all 20 species with abundance 100 in all simulations with $10^4$ samples; SRS (R) with $10^9$-fold more reads fails to achieve the same detection yield (1000 trials, x-axis is $\log_{10}$-scale and jittered). Each sampling depth is depicted in a unique color. b: SQUICH enables detection of small fold changes, here 2 fold in 20 species, in a background of >260,000 species. With $10^5$ samples, all true positives are recovered with 0 false positives. To achieve the same performance with SRS, $10^3$-fold more samples are required (Supplement) (x- and y-values jittered). c: Detection performance of SQUICH and SRS (100 replicates each) in quantifying species across 10 orders of magnitude. 10 species were assigned an abundance of each value (1:10) $10^{0.9}$; and the remaining ~3000 species were set to background level of 100. Yellow bars denote the 25-75th quantiles of measurement for SQUICH and SRS; SQUICH enables detection of small and large molecular abundances across a dynamic range of 10 orders of magnitude with 100,000 samples (top L). At this depth, more than half of species drop-out of SRS sampling and log MSE error is More than 10^10 samples are required by SRS to achieve the same rates of drop-out and log MSE is roughly 2× SQUICH at this depth.

Figure 20:
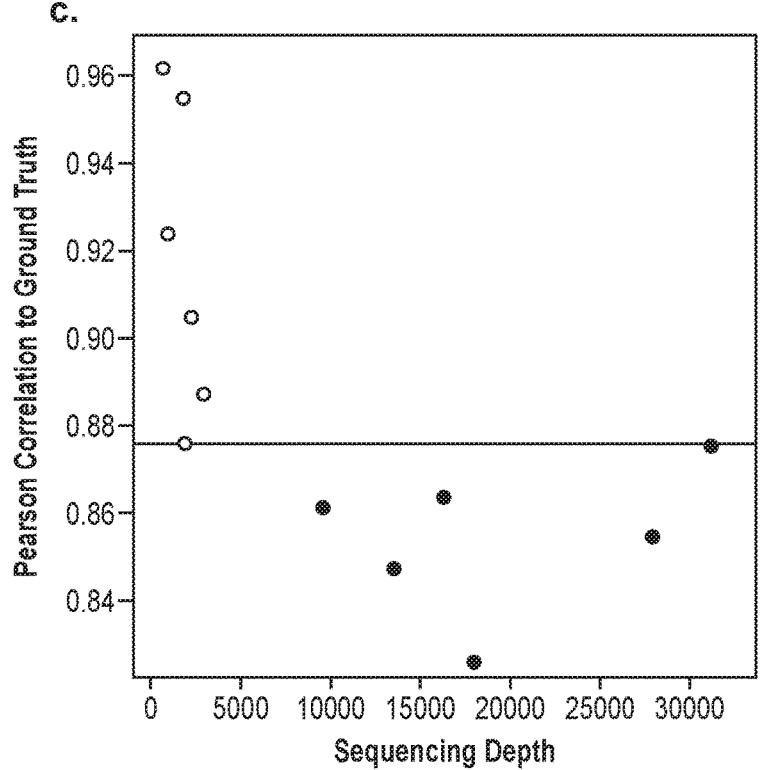

FIG. 20 provides: Six SQUICH replicates were sequenced at depths from 1583 to 3305; six conventional sequencing replicates were sequenced to depths of an average of 9 fold greater, from 10345 to 57213 reads. (a) Example of sequencing reads in each code round by SQUICH and SRS (best representative experiment collapsed over two technical replicates for SQUICH and SRS shown); (b) Pearson correlation between estimated counts and ground truth of each SQUICH replicate exceeded each replicate of conventional sequencing although the correlation in one replicate of SQUICH (depth 2407) exceeded the best conventional library (depth 30653) by only ~0.00015.

DEFINITIONS

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; and, amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups or are functionalized as ethers, amines, or the likes.

The term "oligonucleotide" as used herein denotes a single-stranded multimer of nucleotides of about 2 to 200 nucleotides, up to 500 nucleotides in length. Oligonucleotides may be synthetic or may be made enzymatically, and, in some embodiments, are 20 to 150 nucleotides in length. Oligonucleotides may contain ribonucleotide monomers (i.e., may be oligoribonucleotides) or deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example. Oligonucleotides may contain nucleotide analogs and modified backbones, for example.

The term "primer" as used herein refers to an oligonucleotide that is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be single-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence or fragment, the oligonucleotide primer typically contains 10-25 or more nucleotides, although it may contain fewer or more nucleotides. The primers herein are selected to be substantially complementary to a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

The term "hybridization" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions includes hybridization at about 42C in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by, e.g., Illumina, Life Technologies, and Roche etc. Next-generation sequencing methods may also include nanopore sequencing methods or electronic-detection based methods such as, e.g., Ion Torrent technology commercialized by Life Technologies.

The term "duplex," or "duplexed," as used herein, describes two complementary polynucleotides that are base-paired, i.e., hybridized together.

The terms "determining," "measuring," "evaluating," "assessing," "assaying," and "analyzing" are used interchangeably herein to refer to forms of measurement, and include determining if an element is present or not. These terms include both quantitative and/or qualitative determinations. Assessing may be relative or absolute.

The term "terminal nucleotide", as used herein, refers to the nucleotide at either the 5' or the 3' end of a nucleic acid molecule. The nucleic acid molecule may be in double-stranded form (i.e., duplexed) or in single-stranded form.

The term "ligating", as used herein, refers to the enzymatically catalyzed joining of the terminal nucleotide at the 5' end of a first DNA molecule to the terminal nucleotide at the 3' end of a second DNA molecule.

The terms "plurality", "set" and "population" are used interchangeably to refer to something that contains at least 2 members. In certain cases, a plurality may have at least 10, at least 100, at least 1000, at least 10,000, at least 100,000, at least $10^6$, at least $10^7$, at least $10^8$ or at least $10^9$ or more members.

An "oligonucleotide binding site" refers to a site to which an oligonucleotide hybridizes in a target polynucleotide or fragment. If an oligonucleotide "provides" a binding site for a primer, then the primer may hybridize to that oligonucleotide or its complement.

The term "separating", as used herein, refers to physical separation of two elements (e.g., by size or affinity, etc.) as well as degradation of one element, leaving the other intact.

The term "reference chromosomal region," as used herein refers to a chromosomal region of known nucleotide sequence, e.g., a chromosomal region whose sequence is deposited at NCBI's Genbank database or other databases, for example.

The term "strand" as used herein refers to a nucleic acid made up of nucleotides covalently linked together by covalent bonds, e.g., phosphodiester bonds.

In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "extending", as used herein, refers to the extension of a primer by the addition of nucleotides using a polymerase. If a primer that is annealed to a nucleic acid is extended, the nucleic acid acts as a template for an extension reaction.

The term "in series" is intended to refer to steps that are performed one after the other, on the same sample, i.e., not multiple aliquots of a sample.

The term "aliquot" is intended to refer to a portion of a composition. An aliquot can be in the range of 0.5 ul to 10 ul, e.g., 1 ul to 5 ul for example, although other volumes can be employed depending on the scale of an experiment.

The term "barcode sequence" or "barcode", as used herein, refers to a unique sequence of nucleotides that is sufficiently complex to provide information about (e.g., the source of) a sequence that is appended to the barcode. For example, in many embodiments less than 100 oligonucleotide mixtures are used (e.g., up to 10 or up to 20 mixtures) in the method and, as such, the method may use the same number of barcode sequences to identify the mixture. Barcode sequences may be error correcting in some embodiments. A barcode may be at least 2 nucleotides in length (e.g., 2-20 nucleotides).

The term "unique molecular identifier" or UMI refers to a sequence that can be used to identify sequence reads that are derived from the same initial molecule. Such a sequence, alone or in combination with other features of a sequence read, can be used to distinguish between the different molecules that input into an amplification reaction, prior to sequencing. The complexity of a population of unique molecule identifier sequences used in any one implementation may vary depending on a variety of parameters, e.g., the number of molecules in an initial sample and/or the amount of the sample that is used in a subsequent step. For example, in certain cases, the unique molecule identifier may be of low complexity (e.g., may be composed of a mixture of 8 to 1024 sequences). In other cases, the unique molecule identifier may be of high complexity (e.g., may be composed of 1025 to 1M or more sequences). For example, a random sequence (or 4-8 nucleotides in length) can be used in some cases. Unique molecule identifier are described in Casbon et al (Nuc. Acids Res. 2011, 22 e81), among many others.

The term "sample identifier sequence" or "sample index" is a sequence of nucleotides that can be used to identify the source of a target polynucleotide (i.e., the sample from which sample the target polynucleotide is derived). In use, each sample is tagged with a different sample identifier sequence (e.g., one sequence is appended to each sample, where the different samples are appended to different sequences), and the tagged samples are pooled. After the pooled sample is sequenced, the sample identifier sequence can be used to identify the source of the sequences.

The term "hybridizes to" is intended to mean that two sequences have sufficient complementary to hybridize to form a duplex under the conditions used. In some instances, two sequences that hybridize to one another may have perfect complementarity. In other instances, two sequences that hybridize may have one or more mismatches or other destabilizing features that lower the melting temperature of the duplex.

Certain polynucleotides described herein may be referred to by a formula (e.g., "n–$A_1$'"). Unless otherwise indicated the polynucleotides defined by a formula may be oriented in the 5' to 3' direction. The components of the formula, e.g., "$A_1$'" and "B", etc., refer to separately definable sequences of nucleotides within an oligonucleotide, where, unless implicit from the context, the sequences are linked together covalently such that a polynucleotide described by a formula is a single molecule. In many cases the components of the formula are immediately adjacent to one another in the single molecule. Following convention, the complement of a sequence shown in a formula will be indicated with a prime (') such that the complement of sequence "$A_1$" will be "$A_1$'". Moreover, unless otherwise indicated or implicit from the context, a polynucleotide defined by a formula may have additional sequence, a primer binding site, a molecular barcode, a promoter, or a spacer, etc., between any of the required sequences, or outside of the required sequences. For example, an oligonucleotide of formula "n–$A_1$'" may have one or more other sequences (e.g., a primer binding site, or a unique molecule identifier, etc.) that are 3' of sequence $A_1$', between sequence $A_1$' and sequence n, and/or 5' of sequence n.

The term "formula" is intended to refer to a population of oligonucleotides that has a sequence that varies. Variable regions in a formula are described with a subscript numeral. On the other hand, the term "sequence" refers to a specific sequence. In this context, sequences are indicated by letters that are followed by a subscript numeral. For example, "A" is a variable sequence (that is composed of, e.g., sequences $A_1, A_2, A_3, A_4$, etc.), whereas "$A_1$" is a member of A that has a specific sequence. In another example, an oligonucleotide of formula n–$A_1$' has a member of A' (i.e., a specific sequence) and a variable barcode "n".

The term "variable", in the context of two or more nucleic acid sequences that are variable, refers to two or more nucleic acids that have different sequences of nucleotides relative to one another. In other words, if the polynucleotides of a population have a variable sequence or a particular sequence "varies", then the nucleotide sequence of the polynucleotide molecules of the population varies from molecule to molecule. The term "variable" is not to be read to require that every molecule in a population has a different sequence to the other molecules in a population.

The term "target sequence" in the context of a sample that comprises a target sequence, refers to sample that comprises a population of molecules that comprise the target sequence.

The term "concentration" may be relative to something else, absolute or arbitrarily defined (e.g., "10×" or "100×").

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, the some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Reagent Systems

A reagent system for nucleic acid analysis is described herein. In some embodiments, the reagent mix may comprise a plurality of oligonucleotide sets (e.g., at least 2, at least 3, at least 4, at least 5, up to 10 or 20 sets), where each set comprises i. a first detector oligonucleotide that comprises a sequence that is complementary to a target sequence and a barcode that is 5' of the target-complementary sequence (e.g., of formula n-A', where n is the barcode and A' is the target complementary sequence); and ii. a first competitor oligonucleotide that does not comprises the barcode and competes with the first detector oligonucleotide for binding to the target sequence. In the reagent system: i. the concentration of the competitor oligonucleotide is different in each of the oligonucleotide sets; and ii. the barcode sequence is different in each oligonucleotide set and indicates the concentration of the first competitor oligonucleotide in the oligonucleotide set. An example of a reagent system is schematically illustrated in FIG. 17. As shown, the detector oligonucleotides in the first, second and third oligonucleotide sets all hybridize to the same target sequence, as do the competitor oligonucleotides. However, the concentration of the competitor oligonucleotide is different in each set. As shown, the concentration of the competitor oligonucleotide in the third oligonucleotide set is twice the concentration of the competitor oligonucleotide in the second oligonucleotide set, and the concentration of the competitor oligonucleotide in the second oligonucleotide set is twice the concentration of the competitor oligonucleotide in the first oligonucleotide set. The barcodes (barcodes 1, 2 and 3) indicate the concentration of the competitor oligonucleotide in the set. For example, barcode 1 indicates that the competitor oligonucleotide is at concentration of 2, barcode 2 indicates that the competitor oligonucleotide is at concentration of 4 and barcode 3 indicates that the competitor oligonucleotide is at concentration of 8. In some embodiments, the concentrations of the competitor oligonucleotides may increase exponentially in the sets, i.e., there may be a 2-, 5or 10-fold difference between the concentrations of the competitor oligonucleotides in the different sets. As would be apparent, within each set the detector oligonucleotide and the competitor oligonucleotide can have identical or near identical sequences, otherwise the competitor oligonucleotide would not compete for binding to the target with the detector oligonucleotide. Therefore, within each set, the detector oligonucleotide and the competitor oligonucleotide should share a sequence of at least 10, at least 15, at least 20, at least 25 or at least 30 contiguous nucleotides.

As will be explained in greater detail below, the oligonucleotide set may in separate containers (e.g., as separate mixtures, where each container contains an oligonucleotide set), or all mixed together in the same container. In embodiments in which mixtures of the different oligonucleotide sets are in separate containers, the detector oligonucleotides in the different containers can have the same sequence with the exception of the barcode, and the competitor oligonucleotides in the different containers can have the same sequence.

In embodiments in which the different oligonucleotide sets are mixed together in the same container, the sequences that hybridizes to the target sequence in the different oligonucleotide sets may be different in order to allow the different sets of oligonucleotides to hybridize to the target in order by, for example, lowering the temperature of the hybridization. As such, in some embodiments, the detector oligonucleotides and competitor oligonucleotides in some sets may be longer or shorter than others, for example. In some embodiments, in the mixture, the oligonucleotide sets that have a lower concentration of competitor oligonucleotide hybridize to their targets at a higher temperature or faster than the oligonucleotide sets that have a higher concentration of competitor oligonucleotide.

In any embodiment, the detector oligonucleotides should have least 10, at least 15, at least 20, at least 25 or at least 30 contiguous nucleotides in common, and the competitor oligonucleotides should have least 10, at least 15, at least 20, at least 25 or at least 30 contiguous nucleotides in common, across the different sets.

In some embodiments, the reagent system may comprise a plurality of oligonucleotide sets (e.g., at least 2, at least 3, at least 4, at least 5, up to 10 or 20 sets), each set comprising: i. a first detector oligonucleotide, of formula $n-A_1'$; and ii. a first competitor oligonucleotide of sequence $A_1'$; wherein: sequence $A_1'$ of each first detector oligonucleotide and each first competitor oligonucleotide hybridizes to a first target sequence, of sequence $A_1$; the concentration of the competitor oligonucleotide is different in each of the oligonucleotide sets; and sequence n is a barcode sequence that is different in each oligonucleotide set and indicates the concentration of the first competitor oligonucleotide in the oligonucleotide set. Sequence $A_1'$ does not need to be the same in every set. Rather, sequence $A_1'$ may vary from set to set as long it has sufficient complementary to hybridize to sequence target sequence $A_1$. For example, sequence $A_1'$ may be longer in some sets than others or may contain destabilizing mismatches in some sets. In some embodiments, sequence $A_1'$ is the same in all the sets.

In some embodiments, each oligonucleotide set may a separate mixture and, as such, the separate sets may be housed in separate containers. In other embodiments, all of the oligonucleotide sets in the plurality are present in the same mixture. In these embodiments, in the mixture, the oligonucleotide sets that have a lower concentration of competitor oligonucleotide hybridize to their targets at a higher temperature or faster than the oligonucleotide sets that have a higher concentration of competitor oligonucleotide. This may be done by, e.g., increasing the lengths of the A1' sequences or including mismatches or other destabilizing features, as the concentration of the competitor oligonucleotide in the set decreases.

In some embodiments, the system comprises a plurality of oligonucleotide sets (e.g., at least 2, at least 3, at least 4, at least 5, typically up to 10 or 20 oligonucleotide sets), where each oligonucleotide set is in a separate container, e.g., tube or mixed together, as described above. In some embodiments, each oligonucleotide set of the system comprises i. a first detector oligonucleotide, of formula $n-A_1'$ and ii. a first competitor oligonucleotide of sequence $A_1'$ (i.e., an oligonucleotide that contains sequence $A_1'$ but not barcode n), which sequence is identical to the A1' sequence of the first detector oligonucleotide. In each oligonucleotide set: i. sequence $A_1'$ hybridizes to a first target sequence, of sequence $A_1$, e.g., may be the complement of a first target sequence of sequence $A_1$ (where the "'" indicates that the sequence is a complement), ii. the concentration of the competitor oligonucleotide is different in each of the oligonucleotide sets, and iii. sequence n is a barcode sequence that is different in each oligonucleotide set and indicates the concentration of the first competitor oligonucleotide in the oligonucleotide set. For example, if the reagent system comprises only two oligonucleotide sets, then both oligonucleotide sets can potentially contain the same competitor oligonucleotide (of sequence $A_1'$) at different concentrations, and different first detector oligonucleotides, where: i. the first detector oligonucleotide in the first oligonucleotide set contains sequence $A_1'$ as well as barcode $n_1$ (which indicates the concentration of the competitor oligonucleotide in the first oligonucleotide set) and ii. the second detector oligonucleotide in the first oligonucleotide set contains sequence $A_1'$ as well as barcode $n_2$ (which indicates the concentration of the competitor oligonucleotide in the second oligonucleotide set). In any embodiment, a particular detector oligonucleotide can be at approximately the same concentration in each oligonucleotide set.

For example, in some embodiments, the system may comprise: a first oligonucleotide set containing a first detector oligonucleotide, of sequence $n_1-A_1'$ and ii. a first competitor oligonucleotide of sequence $A_1'$ (i.e., an oligonucleotide that contains sequence $A_1'$ but not the barcode n) at a first concentration (where sequence $n_1$ indicates the first concentration), a second oligonucleotide set containing a first detector oligonucleotide, of sequence $n_2-A_1'$ and ii. the first competitor oligonucleotide at a second concentration (where sequence $n_2$ indicates the second concentration), a third oligonucleotide set containing a first detector oligonucleotide, of sequence $n_3-A_1'$ and ii. the first competitor oligonucleotide at a third concentration (where sequence $n_3$ indicates the third concentration), and a fourth oligonucleotide set containing a first detector oligonucleotide, of sequence $n_4-A_1'$ and ii. the first competitor oligonucleotide at a fourth concentration (where sequence $n_4$ indicates the fourth concentration), and so on. The concentrations may increase exponentially, i.e., there may be a 2-, 5- or 10-fold difference between the different concentrations of the competitor oligonucleotide.

In any embodiment, a reagent system may also comprise an oligonucleotide set containing a detector oligonucleotide without a corresponding competitor oligonucleotide. For example, in any embodiment, a reagent system may also comprise a oligonucleotide set containing a first detector oligonucleotide of formula $n-A_1'$ that does not contain a first competitor oligonucleotide. In these embodiments, the barcode sequence n indicates that the first competitor oligonucleotide is not present in the oligonucleotide set.

In some embodiments, the oligonucleotide sets may comprise one or more other competitor oligonucleotide/detector oligonucleotide pairs that recognize (via the sequences of A') other target sequences. For example, in some embodiments, each mixture may further comprise: iii. a second detector oligonucleotide, of formula $n-A_2'$ and iv. a second competitor oligonucleotide, of sequence $A_2'$ (i.e., sequence $A_2'$ but not barcode n). In this embodiment, sequence $A_2'$ hybridizes to a second target sequences of sequence $A_2$, e.g., may have the complement of a second target sequences of sequence $A_2$; sequences $A_1'$ and $A_2'$ are different; and sequence n is a barcode sequence that is different in each oligonucleotide set and indicates the concentration of the second competitor oligonucleotide in the oligonucleotide set. Sequence n in the first and second competitor oligonucleotides may be the same. However, they can be different in some implementations.

The competitor oligonucleotides in the different tubes may be at any suitable concentrations. If all of the nucleotide sets are present in the same container, then the competitor oligonucleotide should be at different concentrations in the mixture. In some embodiments, the competitor oligonucleotides may be 2-fold to 10-fold different from oligonucleotide set to oligonucleotide set, i.e., may be represented by a series of 2×-10× (e.g., 2×, 5× or 10×) increases in concentration. For example, in some embodiments, the competitor oligonucleotide in the first, second, third and fourth oligonucleotide sets may be at a concentration of 1, 10, 100 and 1,000, 1, 2, 4, and 8 or 1, 5, 25 and 125, for example, depending on whether the oligonucleotide sets have a 2-fold, 5-fold or 10-fold difference in concentrations of the competitor oligonucleotide.

The lengths of the various required sequences may vary independently. In some embodiments, the target sequences (or complements thereof) may be at least 8 nucleotides in length, e.g., 10-20 nucleotides in length, whereas barcode n can be as short as a single base and as long as needed. In typical embodiments, the barcode sequences are 2-10 nucleotides in length.

In some embodiments, the detector oligonucleotide(s) may incorporate one or more primer binding sites, such that certain products can be amplified after a reaction has occurred. In certain of these embodiments, the detector oligonucleotide(s) may be of formula p2–n–A', wherein A' is complementary to a target sequences (as described above), n is the barcode (as described above) and p2 provides a primer binding site (which may be in the range of 8-20 nucleotides in length in some cases.

In some embodiments, the sequences of region A' can be complementary to a biological sequence (e.g., cDNA or genomic DNA, etc.) from any species such as a microorganism, a plant or an animal, such as a mammal. In other embodiments, the sequences of region A' are non-biological. In these embodiments, the detector oligonucleotide may be of the formula p2–n–A' or p2–n–A'–p1', as described in the figures.

The detector and/or competitor oligonucleotides may be blocked at the 3' end (i.e., do not contain a 3' hydroxyl) and, in any embodiment, may comprise a UMI (a unique molecule identifier) that is, e.g., 5' of barcode n. In general, the competitor oligonucleotide(s) and the detector oligonucleotide(s) are designed to minimize cross-hybridization (i.e., with each other). Non-cross hybridizing sequences (or "orthogonal") sequences are known and, in some embodiments, at least barcode n and, optionally region A' is composed of only three of G, A, T, and C, e.g., A, T, and C and not G. In many embodiments, the detector oligonucleotides have a 3' hydroxyl that can be extended by a polymerase or by ligation, but the competitor oligonucleotides do not.

In some embodiments, the system may comprise: (a) a first oligonucleotide set that comprises: i. a first detector oligonucleotide, of sequence $n_1-A_1'$; and ii. a first concentration of the first competitor oligonucleotide of sequence $A_1'$; and (b) a second oligonucleotide set that comprises: i. a second detector oligonucleotide, of sequence $n_2-A_1'$; and ii. a second concentration of the first competitor oligonucleotide of sequence $A_1'$. In these embodiments: (i) sequence $A_1'$ is the same in the first and second detector oligonucleotides and the first competitor oligonucleotide; (ii) the concentration of the first competitor oligonucleotide in the second oligonucleotide set is at least 2-fold higher than the concentration of the first competitor oligonucleotide in the first oligonucleotide set; and (iii) barcode sequences $n_1$ and $n_2$ are different and indicate the concentrations of the first competitor oligonucleotides in the first and second oligonucleotide sets, respectively.

In these embodiments, the system may contain additional oligonucleotide sets, each containing different first competitor oligonucleotide (with a different barcode), and different concentrations of the first competitor oligonucleotide. For example, in these embodiments, the reagent system may comprise: (c) a third oligonucleotide set comprising: i. a third detector oligonucleotide, of sequence $n_3-A_1'$, and ii. a third concentration of the first competitor oligonucleotide of sequence $A_1'$. In these embodiments, (i) sequence $A_1'$ is the same in the detector oligonucleotides and first competitor oligonucleotide of (a), (b) and (c); (ii) the concentration of the first competitor oligonucleotide in the third oligonucleotide set is at least 2-fold higher (e.g., at least 5-fold or at least 10-fold higher, etc.) than the concentration of the first competitor oligonucleotide in the second oligonucleotide set; and (iii) barcode sequences $n_1$, $n_2$ and $n_3$ are different and indicate the concentrations of the first competitor oligonucleotides in the first, second and third oligonucleotide sets, respectively.

In some embodiments, the oligonucleotide sets may be multiplexed so that the abundance of multiple target sequences (e.g., at least 2, at least 5, at least 10, at least 50, up to 100, 500 or 1,000 or more) can be detected. In these embodiments, the first oligonucleotide set (of (a)) may further comprise: iii. a third detector oligonucleotide, of sequence $n_1-A_2'$, and iv. a first concentration of a second competitor oligonucleotide, of sequence $A_2'$. In these embodiments, the second oligonucleotide set of (b) further comprises: iii. a fourth detector oligonucleotide, of formula $n_2-A_2'$ and iv. a second concentration of the second competitor oligonucleotide, of sequence $A_2'$. In these embodiments: (i) the concentration of the second competitor oligonucleotide in the second oligonucleotide set is at least 2-fold higher (e.g., at least 5-fold or at least 10-fold higher, etc.) than the concentration of the first competitor oligonucleotide in the first oligonucleotide set, and (ii) barcode sequences $n_1$ and $n_2$, which indicate the concentrations of the second competitor oligonucleotides in the first and second oligonucleotide sets, respectively. As would be apparent, sequences $n_1$ and $n_2$ are different.

In many embodiments, there are less than 100 oligonucleotide oligonucleotide sets (e.g., up to 10 or up to 20 oligonucleotide sets) in a system. The oligonucleotide sets may be aqueous or dried, for example. The various sets may be in separate containers or mixed together. The concentration of each detector oligonucleotide in a oligonucleotide set may be in the range of 0.001 to 10 pM, e.g., 10 fM to 5 pM, although concentrations outside of this range can be used in many applications.

In any embodiment, at least the detector oligonucleotide in each set may be a partially double-stranded toehold oligonucleotide (see, e.g., Byrom et al, Nucleic Acids Res. 2014 42:e120).

In any embodiment, the reagent system may comprise a synthetic oligonucleotide comprising the first target sequence and/or the second target sequence. In some embodiments, the first and/or second target sequence may be a sequence in genomic DNA, RNA or cDNA.

Methods

A method for analyzing a nucleic acid sample is also provided. In some embodiments, the method may comprise:

(a) sequentially hybridizing a plurality of the oligonucleotide sets of the reagent system described above with a sample that comprises a population of molecules comprising the target sequence, wherein the oligonucleotide sets are hybridized in order of increasing concentration of the competitor oligonucleotide; and (b) performing a biochemical reaction on the hybridization product after each oligonucleotide set has hybridized.

In this method, the biochemical reaction may comprise, e.g.: i. extending the hybridized target sequence using the detector oligonucleotides as a template, thereby producing primer extension products that comprise the complement of the barcodes of the hybridized detector oligonucleotides or ii. extending the hybridized detector oligonucleotides using the target sequence as a template, thereby producing primer extension products that comprise the barcodes of the hybridized detector oligonucleotides for example, although other reactions could be performed. This initial part of the method—the part that tags molecules with a barcode based on their abundance—may be referred to as "SQUISH" in other parts of this disclosure.

As noted above, in some embodiment each oligonucleotide set is a separate mixture. In these embodiments, the method may comprise: (a) hybridizing an aliquot of each mixture of oligonucleotides to produce a hybridized sample; (b) performing a biochemical reaction on the hybridized sample of (a); and (c) repeating steps (a) and (b) using a different mixture of oligonucleotides of the reagent system, until all of the mixtures of oligonucleotides have been hybridized to the sample, wherein the mixtures of oligonucleotides used in steps (a) and (c) are added to the sample in order of increasing concentration of the competitor oligonucleotide.

As noted above, in some embodiments, all of the oligonucleotide sets in the plurality of oligonucleotides are mixed together with the sample in a reaction mix. In these embodiments, the oligonucleotide sets that have a lower concentration of competitor oligonucleotide hybridize to their targets at a higher temperature than the oligonucleotide sets that have a higher concentration of competitor oligonucleotide, and the sequential hybridization of the plurality of oligonucleotide sets may be done by lowering the temperature of the reaction mix. In other embodiments, the oligonucleotide sets that have a lower concentration of competitor oligonucleotide hybridize to their targets faster than the oligonucleotide sets that have a higher concentration of competitor oligonucleotide, and the sequential hybridization of the plurality of oligonucleotide sets is done by incubating the reaction mix at a single temperature. In these embodiments the method may employ a thermostable enzyme, e.g., a thermostable polymerase or thermostable ligase.

However the method is performed, the method may comprise quantifying the amount of each barcode, or complement thereof, in the primer extension products, determining the profile of barcode sequences in the products, and quantifying the abundance of a nucleic acid comprising a target sequence in the sample using the profile of barcode sequences or complements thereof.

In some embodiments, this method may comprise (a) hybridizing an aliquot of a mixture of oligonucleotides of a reagent system with a sample that comprises target sequences, to produce a hybridized sample; (b) performing a biochemical reaction on the hybridized sample of (a); and (c) repeating steps (a) and (b) using a different mixture of oligonucleotides of the reagent system until all of the mixtures of oligonucleotides have been hybridized to the sample. Importantly, the mixtures of oligonucleotides of step (a) and the repeats of step (c) should be added to the sample in order of increasing concentration of the competitor oligonucleotide. The total number of times that steps (a) and (b) are performed usually corresponds to the number of barcodes used (which also corresponds to the number of oligonucleotides mixtures that are part of the reagent system) and, as such, those steps may be performed using less than 100 times (typically up to 10 or up to 20 cycles). In some embodiments, the steps may be performed 3-10 times.

Step (b) may be done a variety of different ways.

For example, step (b) can be done by extending the targets using the detector oligonucleotides as a template, thereby producing primer extension products that comprise the complement of the barcodes of the hybridized detector probes. An example of this implementation is schematically illustrated in FIG. 3.

In another example, step (b) can be done by washing away unhybridized detector oligonucleotides and releasing the hybridized detector oligonucleotides, wherein the target sequences are immobilized on a support. An example of this implementation is schematically illustrated in FIG. 4.

In another example, step (b) can be done by ligating an end oligonucleotide (which may be referred to as a ligation probe) onto the hybridized detector oligonucleotides using the target sequences as a splint for the ligation. This way, only hybridized detector oligonucleotides will be ligated to the end oligonucleotide. An example of this implementation is schematically illustrated in FIG. 5.

In another example, step (b) can be done by circularizing the hybridized detector oligonucleotides using a target sequences as a splint for the ligation. This approach, which may involve padlock probes, molecular inversion probes, or another circularization probe, is schematically illustrated in FIG. 6.

In any embodiment, the method may further comprise, after the reaction is completed, quantifying the amount of each barcode, or complement thereof, that has been: i. added to the hybridized detector probes (see FIG. 3), ii. released from the support (see FIG. 4), iii. ligated to the end oligonucleotide (see FIG. 5) or iv. circularized (see FIG. 6). As shown in these figures, the method can be implemented in a way that adds sites for amplification primers (referred to as p1 and p2) to the ends of the products containing the barcodes. This allows the products to be amplified, e.g., by limited cycle PCR that has up to 10 cycles, e.g., 4-8 cycles, prior to analysis, e.g., sequencing. Primer binding sites are not necessary for the method because not all analysis methods, including many sequencing methods, require amplification. In some embodiments, the quantifying may be done by sequencing, qPCR, or by hybridization to an array. In the embodiments shown in FIGS. 3-6, the products may be amplified by PCR and then sequenced using any convenient sequencing platform, e.g., Illumina sequencing. If the products are amplified and sequencing is used to quantify the barcodes, then the detector oligonucleotides may contain a UMI in order to identify redundant sequence reads although, in theory, this method can be done without using a UMI by counting sequence reads alone.

In sequencing embodiments (as illustrated in FIG. 3), the method may comprise: extending the detector oligonucleotides in the hybridization products of (a) to produce primer extension products that comprise the complements of the barcodes; and sequencing at least the complements of the barcodes in the primer extension products, or an amplification product thereof. In these embodiments, the target sequences may be of formula p1–A and the detector oligonucleotides may be of formula p2–n–A', optionally containing a UMI between n and p2, as shown in FIG. 3. In these embodiments, the target sequences are generally non-biological sequences, although their abundance in the sample may represent the abundance of a biological sequence or a binding event to the same.

In other sequencing embodiments (as illustrated in FIG. 4) the method may comprise immobilizing the nucleic acid sample to a support; and, in step (b): hybridizing an aliquot of the plurality of a mixture with the sample, washing the sample to remove unbound material, eluting the detector oligonucleotides that are hybridized to the sample and sequencing the released products, or an amplification product thereof. In these embodiments, the target sequences may be of formula A and the detector oligonucleotides may be of formula p2–n–A'–p1', optionally containing a UMI between n and p2, as shown in FIG. 4. In these embodiments, the target sequences may be biological or non-biological.

In other sequencing embodiments (as illustrated in FIG. 5), the method may comprise ligating an end oligonucleotide onto an end of the detector using a target sequence as a splint; and sequencing the ligation products, or an amplification product thereof. In these embodiments, the target sequence may be of formula A, the detector oligonucleotides may be of formula p2–n–A', optionally containing a UMI between n and p2, and the end oligonucleotide is splinted with the detector oligonucleotide by the target sequence, as shown in FIG. 5. In these embodiments, the target sequences may be biological or non-biological.

In other sequencing embodiments (as illustrated in FIG. 6), the method may comprise circularizing the detector oligonucleotides using a target sequence as a splint and sequencing the circularized products, or an amplification product thereof. As shown, in these embodiments, the detector oligonucleotides may be of formula aA'–p1'–spacer–p2–n–A', where aA' is adjacent to A' in the target sequence, optionally containing a UMI between n and p2, as shown. In these embodiments, the target sequences may be biological or non-biological.

Figure 2:
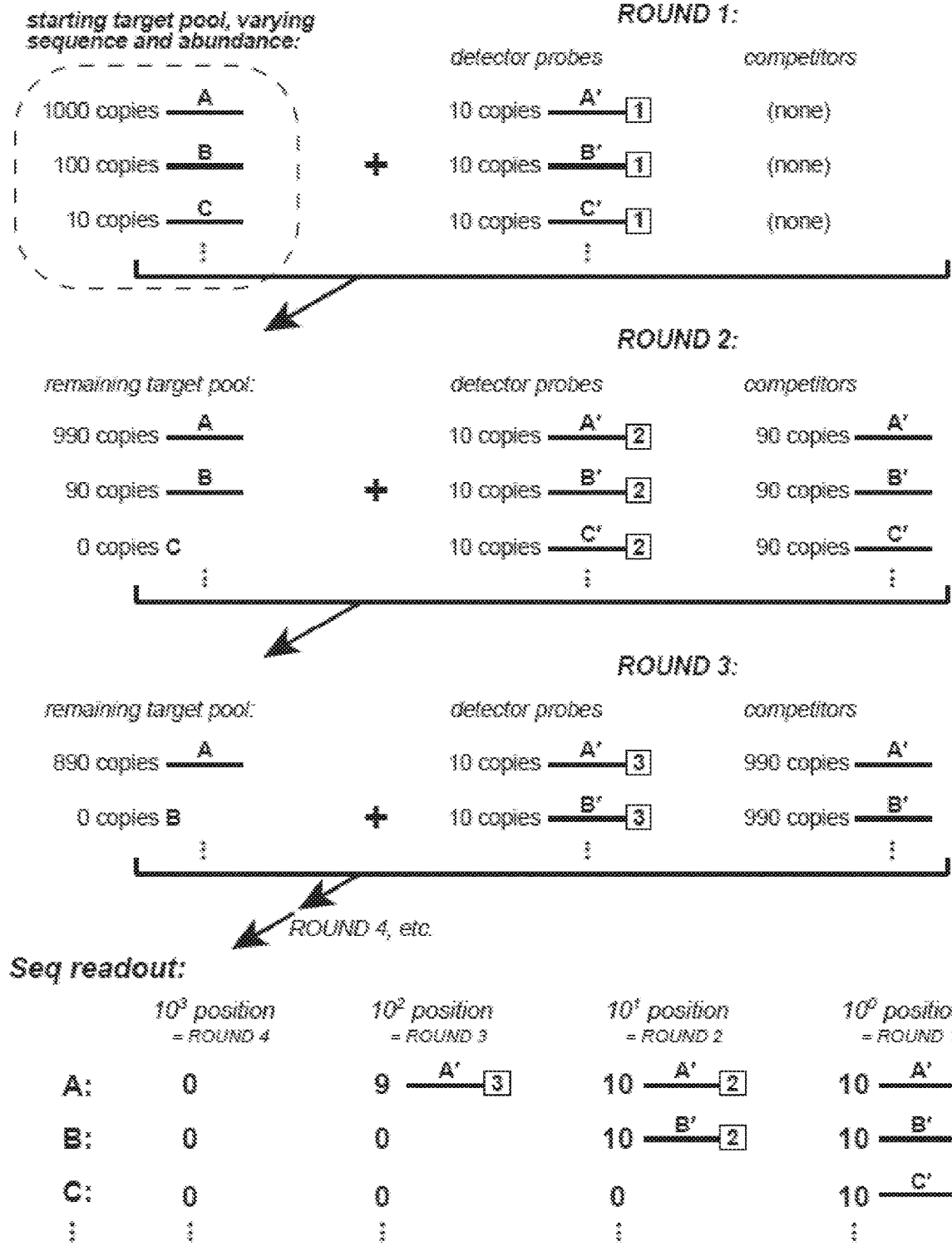
FIG. 2 shows the generalized scheme of an embodiment of the present method. A pool of sequences of varying abundances is subject to cumulative interaction with probe and competitor oligonucleotides that can interact with specific targets in the pool. The probes are tagged with sequences ("round-codes", depicted here as numbered boxes) that identify which round they were deployed. The amount of competitors increases, e.g. exponentially, with every round, and the accumulated interaction with probes and competitors will eventually exhaust the corresponding target from the pool. The products of the interaction of probes with targets are designed to be selectable, for example by PCR amplification, resulting in a pool of probes whose abundance is a mathematical transformation of the abundances of the pool of targets. Finally, the relative abundance of the selected probes is read out by high-throughput sequencing ("Seq"), and estimates of the original target abundances can be reconstructed mathematically. Much of this figure is exemplary only, and the method can be further generalized. For example, there are a number of ways in which the probe interaction with target can be made selectable. The scaling with each round may be any factor, not necessarily powers of 10 as shown; indeed, the factor may be chosen to vary with each round and/or for each target. The number of probe molecules per round may be increased (providing better accuracy). The probes may be designed to report on not just a single target but a summation of targets.

As illustrated, in FIG. 2, the method may comprise determining the profile of barcode sequences in the products, i.e., determining how many molecules comprising barcode $n_1$ or complement thereof were produced, how many molecules comprising barcode $n_2$ or complement thereof were produced, how many molecules comprising barcode $n_3$ or complement thereof were produced, how many molecules comprising barcode $n_4$ or complement thereof were produced, and how many molecules comprising barcode $n_5$ or complement thereof were produced, etc. As shown in FIG. 2, the abundance of a nucleic acid comprising a target sequence in the sample can be quantified based on the profile of barcode sequences or complements thereof.

FIG. 1 provides a hypothetical comparison of the present method with a conventional sequencing method, for quantifying expression of two gene products.

As noted above, the target sequences can be biological (in which case they already vary in abundance from molecule to molecule) or non-biological. If the target sequences are non-biological, then they may represent the abundance of biological sequences, binding events to the same, or sequences that have been enriched via an assay. Such target sequences may be produced by obtaining probes that contain i. a target sequence and ii. a selection sequence or a binding agent comprising the same, wherein the probes contain a cleavable linkage, e.g., a uracil, between the target sequence and the selection sequence, selecting for probes that contain a specific selection sequence or a binding agent comprising the same (e.g., by hybridization, binding or by enrichment in an assay) releasing the target sequence from the selected probes by cleaving the cleavable linkage. FIG. 7 generally shows how target sequences can be produced. In these embodiments, the probes have a cleavable linkage "U" between the target sequence (indicated by, e.g., tc-A) and the selection sequence (indicated by, e.g., A'). FIG. 8 illustrates how target sequences whose abundance correlates with biological nucleic acids can be generated. FIG. 9 illustrates how target sequences whose abundance correlates with antibody binding events can be generated. In some embodiments and as illustrated in FIGS. 7-9), the probes are of formula X—U-A, where X hybridizes to a sequence in a biological sample or is an antibody that binds to an epitope in the biological sample, U comprises a cleavable linkage and A is a target sequence. The non-biological target sequences in this method may be used in conjunction with a look-up table that allows one to identify which biological sequence/antibody corresponds to which target sequence.

FIGS. 10-16 illustrate several additional embodiments or features that can be employed herein. As illustrated in FIG. 10, the initial steps of present method can be implemented in a single tube reaction, without adding additional reagents during the course of the rejection, i.e., in a "one-pot" reaction. As shown, this can be done by ramping the temperature of the incubation. One approach to perform the initial steps of the method without sequentially adding barcoded detectors into the tube would rely on changing the temperature. In this embodiment, round-one detector to have the highest Tm, round-two detector have a lower Tm, and round-three detector would have the lowest Tm, etc. The different competitors corresponding to detectors that have the same Tm as the detectors, for example round-one detector has the highest Tm value, and round-two detector has few degree lower Tm and its competitor 2 is also designed to have equal Tm, likewise to round-three detector and its competitor 2 etc. The reaction could start at a high temperature as the Tm of round-one detector, at which only round-one detector could hybridize to the target. By incubating this reaction at this temperature briefly, with enzymatic polymerization target sequence can take the detector as template and extend. The competitors and other codes would not be able to hybridize at this temperature because their Tm's are lower. Then, the temperature would be decreased to the Tm of round-two detector and competitor 2, allowing round-two detector and its competitor 2 to hybridize to the target and then target to be extended, and so on until the lowest Tm of the last pair of detector and competitors is reached. The end result would be the same as that of the other embodiment (i.e., the embodiment in which the next set of oligonucleotides are added after a certain amount of time) but the hands-on time and error introduced by sequential addition of detector/competitor oligonucleotides would be avoided. This approach can also be modified by designing and utilizing a competitor of the same Tm as the round-one detector. Note that at equilibrium (shown in FIG. 10), even without a temperature ramp, targets should be occupied by the detector and competitor oligonucleotides in a prespecified order dictated by the change in energy between single and duplexed states. As such, the encoding part of the method can be implemented in a one pot reaction without a change in temperature.

FIG. 11 shows how toehold exchange probes (see, e.g., Zhang, Chen, and Yin (2012) "Optimizing the specificity of nucleic acid hybridization," *Nature Chemistry*. DOI: 10.1038/NCHEM.1246) can be used. Under certain conditions, detectors and competitors can be driven to hybridize with targets because there is an enthalpic reward for each correct base-pairing. This design, however, also causes slightly mismatched duplexes to be enthalpically favorable over oligonucleotides remaining in their original unpaired states. Slightly mismatched duplexes, such as one or two mismatches can potentially overwhelm the correct pairs, resulting in inaccurate detection. To correct for this, one could increase the specificity of base-pairing using foothold exchange probes. Specifically, each detector and each competitor can be duplexed ahead of time with a "protector" oligonucleotide, in such a way that a single-stranded toehold would still be free for the target to hybridize, forming the detector/competitor duplex. As the double arrows in FIG. 11 suggest, the two states are almost equally populated because there is virtually no energetic change as the reaction progresses (i.e. $\Delta G=0$). This is possible because there are as many bonds broken as formed ($\Delta H=0$) and the number of molecules is constant ($\Delta S=0$). Given this equilibrium, a detector that forms even a slightly mismatched duplex will push the reaction back toward the detector/protector state, thus strongly discouraging mismatches. This state of equilibrium could seem counterproductive to the present method, namely to get the detectors hybridized to targets. However, by extending the targets on the detector in the polymerization steps of the present method, the reaction should be driven forward by Le Chatelier's principle. This concept of toehold exchange protectors can be implemented by designing protector oligonucleotides specific to each detector and each competitor, as shown in FIG. 11. The detector/protector and competitor/protector duplexes would be annealed ahead of time, and then the duplexes would be added to the reaction in the same way that detectors and competitors were previously added.

FIG. 12 shows how the present method can detect small changes in the amount of a target sequence in a sample. In biological or chemical quantification or screening, it is desired to measure small absolute molecular changes between different conditions, and small molecular difference in a complex of biosamples. For the intended purpose herein the SQUISH can be modified as: a) hybridizing an aliquot of competitor reagent with a sample that comprises targets of interest present with small fold change or small difference of absolute molecular numbers; b) performing the standard SQUISH procedure to complete the quantification.

FIG. 13 shows how competitors can be generated by hybridization to a biological sample (e.g., by enriching for oligonucleotides that hybridize to a sample or by extending primers that hybridize to a sample, for example) and then used in the present method to detect very low abundance sequences in a sample, e.g. regions of a chromosome that are deleted or expressed at a very low abundance. In this implementation, levels of all molecular species of interest are first converted into abundance of competitors (by, e.g., hybridization to the sample) and a target library composed of various sequences at equal abundance is designed; next, a single round of the present method is run on this designed target pool, using the detectors and competitors generated above. Because these competitors specifically block their complementary targets in the target pool, the abundance of individual competitors—representing the abundance of corresponding molecular species in the given samples—determines how much of specific targets are left for the detectors. In other words, the highly abundant competitors, derived from highly abundant molecular species of interest, should result in low-abundance targets for detectors. Likewise, the less abundant competitors spare more targets for detectors, thus generating higher signals with the other approaches. In effect, this implementation enables the detection of low-abundance molecules, even deletions or dropouts, while eliminating all the high-abundance sequences. In some embodiments, the rounds of hybridization can also be performed sequentially, e.g. allowing generated competitors to first react with the target library, followed by detection with detectors.

FIGS. 14 and 15 shows an embodiment in which the molecules that are bound by the competitor oligonucleotides can be amplified and analyzed. In the embodiment, competitors with increasing amounts between rounds compete out certain amounts of various molecules using approaches of hybridization and round-specific barcodes. Though these competed-out molecules are usually discarded, they can actually contain rich molecular information in a given sample. Such rich information can be captured by introducing a competitor-specific PCR handle, so if desired the molecules of interest can be recovered by using competitor- and target-specific PCR handles. This enables custom sequencing designs that enrich a pool of molecules at a chosen strata of abundance, i.e., sequencing only targets at abundance at least x and no more than y of them.

FIG. 16 shows how a mismatch-specific oligonucleotide can increase detection accuracy. Some embodiments of the present method requires accurate and full complementary hybridization between molecular targets of interest and competitors, and molecular targets of interest and detection probes. To achieve this, the sample can be treated with a mismatch-specific endonuclease after the encoding step and prior to PCR enrichment. This endonucleolytic digestion efficiently cuts at any mismatched site of double-stranded DNA, therefore breaking the PCR handles required for the downstream PCR amplification. As a result, partially hybridized molecules will not be sequenced, or the probability of sequencing a target should decrease with the number of mismatches to the code and competitor.

Utility

The present method may be used in a wide variety of applications including, but not limited to the analysis of polymorphisms and gene expression, identification of guide RNAs in activity screens of CRISPR/Cas9 variants, combinatorial chemistry, phage display (or any similar library), metagenomics, and the examination of proteins (if the target sequences are initially conjugated to antibodies). Any biological sample could be analyzed using the method described above, including tissue samples (if the target sequences are conjugated to antibodies, or DNA/RNA from prokaryotes and eukaryotes, including yeast, plants and animals, such as fish, birds, reptiles, amphibians and mammals. In certain embodiments, the DNA or may be from mammalian cells, i.e., cells from mice, rabbits, primates, or humans, or cultured derivatives thereof.

Kits

Also provided by this disclosure are kits that contain the reagents, as described above. In addition to the above-mentioned components, the subject kit may further include instructions for using the components of the kit to practice the present method.

EMBODIMENTS

Embodiment 1. A reagent system for nucleic acid analysis, comprising: a plurality of mixtures each comprising: i. a first detector oligonucleotide, of formula n-$A_1$'; and ii. a first competitor oligonucleotide of sequence $A_1$', wherein: sequence $A_1$' is the complement of a first target sequence of sequence $A_1$; the concentration of the competitor oligonucleotide is different in each of the mixtures; and sequence n is a barcode sequence that is different in each mixture and indicates the concentration of the first competitor oligonucleotide in the mixture.

Embodiment 2. The reagent system of embodiment 1, wherein each mixture further comprises: iii. a second detector oligonucleotide, of formula n–$A_2$'; and iv. a second competitor oligonucleotide, of sequence $A_2$'; wherein: sequence $A_2$' is the complement of a second target sequence of sequence $A_2$; sequences $A_1$' and $A_2$' are different; and sequence n is a barcode sequence that is different in each mixture and indicates the concentration of the second competitor oligonucleotide in the mixture.

Embodiment 3. The reagent system of any prior embodiment, wherein the concentrations of the competitor oligonucleotide are at least 2-fold different from mixture to mixture.

Embodiment 4. The reagent system of any prior embodiment, wherein the detector oligonucleotide(s) are of formula p2–n–A', wherein A' is complementary to a target sequences, n is the barcode and p2 provides a primer binding site.

Embodiment 5. The reagent system of any prior embodiment, wherein the detector oligonucleotide(s) are blocked at the 3' end.

Embodiment 6. The reagent system of any prior embodiment, wherein the detector oligonucleotide(s) comprise a UMI (unique molecule identifier).

Embodiment 7. The reagent system of any prior embodiment, wherein the competitor oligonucleotide(s) and the detector oligonucleotide(s) are designed to minimize cross-hybridization.

Embodiment 8. The reagent system of any prior embodiment, wherein at least barcode n and, optionally region A' is composed of only three of G, A, T, and C.

Embodiment 9. The reagent system of any prior embodiment, wherein at least barcode n and, optionally region A' is composed of A, T, and C and not G.

Embodiment 10. The reagent system of any prior embodiment, the system comprises: (a) a first mixture that comprises: i. a first detector oligonucleotide, of sequence $n_1$–$A_1$'; and ii. a first concentration of the first competitor oligonucleotide of sequence $A_1$'; and (b) a second mixture that comprises: i. a second detector oligonucleotide, of sequence $n_2$–$A_1$'; and ii. a second concentration of the first competitor oligonucleotide of sequence $A_1$'; wherein: (i) sequence $A_1$' is the same in the first and second detector oligonucleotides and the first competitor oligonucleotide; (ii) the concentration of the first competitor oligonucleotide in the second mixture is at least 2-fold higher than the concentration of the first competitor oligonucleotide in the first mixture; and (iii) barcode sequences $n_1$ and $n_2$ are different and indicate the concentrations of the first competitor oligonucleotides in the first and second mixtures, respectively.

Embodiment 11. The reagent system of embodiment 10, wherein the system comprises: (c) a third mixture comprising: i. a third detector oligonucleotide, of sequence $n_3$–$A_1$'; and ii. a third concentration of the first competitor oligonucleotide of sequence $A_1$'; wherein (i) sequence $A_1$' is the same in the detector oligonucleotides and first competitor oligonucleotide of (a), (b) and (c); (ii) the concentration of the first competitor oligonucleotide in the third mixture is at least 2-fold higher than the concentration of the first competitor oligonucleotide in the second mixture; and (iii) barcode sequences $n_1$, $n_2$ and $n_3$ are different and indicate the concentrations of the first competitor oligonucleotides in the first, second and third mixtures, respectively.

Embodiment 12. The reagent system of embodiment 10, wherein: the first mixture of (a) further comprises: iii. a third detector oligonucleotide, of sequence $n_1$-$A_2$'; and iv. a first concentration of a second competitor oligonucleotide, of sequence $A_2$'; and the second mixture of (b) further comprises: iii. a fourth detector oligonucleotide, of formula $n_2$-$A_2$'; and iv. a second concentration of the second competitor oligonucleotide, of sequence $A_2$'; wherein: (i) the concentration of the second competitor oligonucleotide in the second mixture is at least 2-fold higher than the concentration of the first competitor oligonucleotide in the first mixture; and (ii) barcode sequences $n_1$ and $n_2$ indicate the concentrations of the second competitor oligonucleotides in the first and second mixtures, respectively.

Embodiment 13. A method for analyzing a nucleic acid sample, comprising: (a) hybridizing an aliquot of a mixture of oligonucleotides of a reagent system of any prior embodiment with a sample that comprises target sequences, to produce a hybridized sample; (b) performing a biochemical reaction on the hybridized sample of (a); and (c) repeating steps (a) and (b) using a different mixture of oligonucleotides of the reagent system until all of the mixtures of oligonucleotides have been hybridized to the sample, wherein the mixtures of oligonucleotides used in steps (a) and (c) are added to the sample in order of increasing concentration of the competitor oligonucleotide.

Embodiment 14. The method of embodiment 13, wherein step (b) comprises: extending the targets using the detector oligonucleotides as a template, thereby producing primer extension products that comprise the complement of the barcodes of the hybridized detector probes; washing away unhybridized detector oligonucleotides and then releasing the hybridized detector oligonucleotides, wherein the target sequences are immobilized on a support; ligating an end oligonucleotide onto the hybridized detector oligonucleotides using the target sequences as a splint for the ligation; or circularizing the hybridized detector oligonucleotides using a target sequence as a splint for the ligation.

Embodiment 15. The method of embodiment 13 or 14, further comprising, after step (c), quantifying the amount of each barcode, or complement thereof, that has been: i. added to the hybridized detector probes, ii. released from the support, iii. ligated to the end oligonucleotide or iv. circularized.

Embodiment 16. The method of any of embodiments 13-15, wherein the quantifying is done by sequencing, qPCR, or by hybridization to an array.

Embodiment 17. The method of any of embodiments 13-16, wherein the method comprises: extending the detector oligonucleotides in the hybridization products of (a) to produce primer extension products that comprise the complements of the barcodes; and sequencing at least the complements of the barcodes in the primer extension products, or an amplification product thereof.

Embodiment 18. The method of any of embodiment 13-16, wherein the method comprises: immobilizing the nucleic acid sample to a support; and step (b) comprises: hybridizing an aliquot of the plurality of a mixture with the sample; washing the sample to remove unbound material; eluting that detector oligonucleotides that hybridized to the sample; and sequencing the released products, or an amplification product thereof.

Embodiment 19. The method of any of embodiments 13-15, wherein the method comprises: ligating an end oligonucleotide onto an end of the detector using a target sequence as a splint; and sequencing the ligation products, or an amplification product thereof.

Embodiment 20. The method of any of embodiments 13-15, wherein the method comprises: circularizing the detector oligonucleotides using a target sequence as a splint; and sequencing the circularized products, or an amplification product thereof.

Embodiment 21. The method of any of embodiments 13-20, wherein the method further comprises: determining the profile of barcode sequences in the products.

Embodiment 22. The method of embodiment 21, wherein the method further comprises: quantifying the abundance of a nucleic acid comprising a target sequence in the sample based on the profile of barcode sequences or complements thereof.

Embodiment 23. The method of any of embodiments 13-22, wherein the nucleic acid sample is produced by: obtaining probes that contain i. a target sequence and ii. a selection sequence or a binding agent comprising the same, selecting for probes that contain a specific selection sequence or a binding agent comprising the same; and releasing the target sequence from the selected probes.

Embodiment 24. The method of embodiment 23, wherein the probes are of formula X—U-A, X hybridizes to a sequence in a biological sample or is an antibody that binds to an epitope in the biological sample, U comprises a cleavable linkage and A is a target sequence.

EXAMPLES

Next-generation sequencing enables measurement of chemical and biological signals at high throughput and falling cost. Conventional sequencing requires increasing sampling depth to improve signal to noise discrimination, a costly procedure that is also impossible when biological material is limiting. We introduce a new general sampling theory, Molecular Entropy encodinG (MEG), which uses biophysical principles to functionally encode molecular abundance before sampling. SeQUential DepletIon and enriCHment (SQUICH) is a specific example of MEG that, in theory and simulation, enables sampling at a logarithmic or better rate to achieve the same precision as attained with conventional sequencing. In proof-of-principle experiments, SQUICH reduces sequencing depth by a factor of 10. MEG is a general solution to a fundamental problem in molecular sampling and enables a new generation of efficient, precise molecular measurement at logarithmic or better sampling depth.

To illustrate the general theory, we start with a simple stylized example (Example 1) of SeQUential DepletIon and enriCHment (SQUICH), a special case of MEG. Consider a tube containing 10 cubes and $10^4$ spheres (FIG. 18); these quantities are unknown to the experimenter who wants to estimate them. Suppose there is a physical process that for any number n allows up to, but no more than, n shapes of each type to be drawn from the tube. SQUICH uses this procedure as follows: in the first round of SQUICH, one object of each shape (cube and sphere) is captured from the tube, tagged with a "1", and placed into a container we call the sampling box. Then, up to 9 of each shape are captured and destroyed. In the second round of SQUICH, 1 (or 0) of each shape is captured and tagged with a "2" and added to the sampling box. In this example, no cubes are captured, as they have all been removed. Then, up to 89 of each shape are captured and destroyed. The numbers of captured and destroyed molecules in the second round satisfy the property that up to and including this round, $10^2$ (1+9+1+89=100) of each shape has been destroyed or captured. In the third round, 1 (or 0) of each shape is captured, tagged with a "3", and up to 899 of each shape are destroyed; in round 4, one more shape is captured and up to 8999 are destroyed. At the end of 4 rounds, there are 4 cubes and 1 sphere in the sampling box and they are each labeled with the number of the round they were captured in. The abundance of each shape in the original tube can now be estimated with 5 samples without replacement, while SRS requires on the order of $10^2$ to make the same inference.

SQUICH is much more general than as presented in Example 1; MEG is yet more general than SQUICH (Methods and Supplement). The numbers in Ex. 1 were arbitrary: the same procedure can operate on, e.g., $10^{15}$ cubes, allowing a much larger savings in sampling and demonstrating the intuition for why SQUICH enables logarithmic sampling depth compared to SRS.

Informally, three properties enable sampling reductions by SQUICH in Example 1: (1) tagging and removal operating independently on each shape; (2) limiting the number of each shape that is tagged and depleted in each round; (3) sampling only tagged shapes.

The critical properties (1-3) above are fulfilled with nucleic acids replacing the objects of different shapes. Each "shape" in Ex. 1 is replaced by a unique DNA sequence called a target. For each target, sets of DNA oligonucleotides called encoders and competitors that each hybridize with targets are the key to SQUICH. Encoders are libraries of reverse complements of all possible targets which have three critical regions: (1) a region of reverse complementarity to the target; (2) a DNA sequence that is a DNA code representing the round in which the encoder was added to the original tube and; (3) a PCR handle that allows sampling of only targets that extend on encoders. Competitors have the same region of reverse complementarity as encoders, but lack a PCR handle. In each round, targets are hybridized with competitors and encoders, and after hybridization, extend on competitors and encoders (in which case the target is said to be "coded") which serve to tag and pull targets into the sampling box as the physical device did for shapes in Example 1 (Figure S4).

As in Example 1, competitors and encoders are added in limiting amounts (n) at each step so that removal and/or tagging of no more than n of each sequence type can occur in each step. To ensure only coded molecules are sampled, PCR is used as an AND logic gate to selectively sample molecules that are targets AND have extended on encoders (Methods). Competitors can be designed so that targets extending on them can be later retrieved. If targets are in excess of encoders and competitors, the number of targets that extend is limited by the available encoder and competitors. When encoders and competitors are in excess of targets, they compete for binding, which enables estimation of the first significant figures in scientific notation (Results).

In addition, the abundance of each competitor and encoder can vary by target as may be desired in certain applications; for example if an experimenter seeks to measure spheres only if they are more abundant than $10^4$ copies, $10^4$ competitors for spheres could be added in the first round.

Results

SQUICH is simple to embody in experiment and provably enables logarithmic or even sub-logarithmic sampling compared to SRS for precision desired in ubiquitous sequencing applications including estimation of scientific figures formalized in this: Claim (Logarithmic sampling with non-filtered round coding): Suppose the abundance of two species are respectively $x_1 10^{y_1}$ and $x_2 10^{y_2}$ with $y_1 < y_2$ and $x_1, x_2 \in \mathbb{Z}$ and $0<p<1$ fixed. There is a SQUICH procedure such that $((y_2+1)/(y_1))\log(1/p)$ samples suffice to achieve a probability of detection of at least p; a standard result shows SRS requires at least $10^{y_2-y_1}$ samples to detect the second species which implies the sampling depth required by SQUICH is logarithmic compared to SRS.

The proof of the claim shows how SQUICH can achieve more general sampling reductions such as sub-logarithmic rates with super-geometric increases in the number of competitors per round. Simulation tests of SQUICH performance are given in three common application regimes: (1) detection of rare species in the presence of a large background; (2) small fold changes in a complex population; (3) quantification of each species in a population with high dynamic ranges.

To conservatively model SQUICH performance in simulation, a set of engineered DNA target sequences (which are termed "CGA libraries" of length n) consisting of any molecule matching the format [(C/G)A^n] were introduced; CGA libraries are targets behave like the shapes did in Example 1. Competitors and encoders for CGA libraries consist of all reverse compliments of the CGA library with auxiliary sequences that identify them as competitors or encoders (described above, Methods). Equilibrium thermodynamics of CGA are modeled in simulations to include inefficiencies and mismatches in oligonucleotide hybridization when the minimum edit distance between targets is one (Wang & Zhang, 2015; Zhang, Chen, Yin, 2012)(Methods). SQUICH can perform more favorably than in the simulation when targets have minimum edit distance of four or more, a design achieved with sphere packing theory (Conway & Sloane, 2011); that is, CGA codes are a convenient way to explain, model and experimentally embody SQUICH, but SQUICH performance is optimized by different designs of targets. For example, experiments in this paper were performed with oligonucleotides containing degenerate bases (Methods).

Simulation 1 models the "needle in haystack" problem with two species at abundance $10^x$ where x=15, with 20 "needle" species at abundance 100. As predicted by theory, SQUICH robustly identifies all needles across all trials with less than 2000 samples (FIG. 19a). SRS detects at most one needle with $10^{11}$ samples in 1000 simulations and requires more than $10^{15}$ samples for the same recall as achieved by SQUICH with 2000 samples (basic statistical theory). For x=15, this implies SQUICH reduces sampling depth by a factor of 10.

Simulation 2 tests SQUICH performance where a subset of species (here 20) are 2-fold more abundant than a background of complexity >260,000, modeling complexity needed to detect duplication events of >~10 kb in the human genome, or a 2-fold enrichment in a chemical or high throughput pooled CRISPR screen. A statistical estimator for SQUICH to identify species enriched above background was designed (Methods). With this estimator, $10^5$ samples suffice for recovering a median of 18 of the 20 enriched species with 0 false positives (FP) across 1000 trials. To achieve a zero FP rate, SRS requires $10^8$ samples, requiring at least $10^3$-fold higher sampling depth than SQUICH (FIG. 2b). This simulation demonstrates that SQUICH provides flexibility by designing encoder and competitor abundance increases over rounds. Varying competitor and encoder abundance tunes false positive and false negative rates separately, overcoming an intrinsic limitation of SRS where false positives are functionally related to false negatives as a function of sampling depth.

To simulate measurement of native molecules such as RNA or microbial DNA with high dynamic ranges, each RNA species was modeled as a specific CGA code. The molecular biological procedure for converting RNA, DNA or protein to CGA codes is straightforward. In Simulation 3, the performance of SQUICH when the distribution of sampled species fills a high dynamic range ($x10^y$ for x=1, . . . , 9 and y=0, . . . , 9), as arises in measurement of protein and environmental microbial DNA, was tested. SQUICH fails to detect only 428 of more than 5000 species at a sampling depth by $10^5$ (FIG. 19c); SRS has a drop-out of 3706 species. The log MSE log for SQUICH is lower than SRS at depths up to and including $10^{10}$. SQUICH performance with $10^6$ samples also exceeds SRS at depth $10^{11}$; at this depth for SQUICH, a mean of only 4 molecules dropout of sampling.

The study also simulated sequencing of single cells with a dynamic range of transcripts with ~4000 transcripts expressed, and ~1500 transcripts significantly above basal expression which was set to 100 (n=2236), including expression of 10 transcripts at each value $x10^y$ for x=1, . . . , 9 and y=0, . . . , 4, and 100 additional transcripts at each level 1:10. With $10^5$ samples, SQUICH has comparable performance to SRS with $10^7$ samples as measured by drop-out (~2%) and log MSE a significant improvement over high dropout rates in single-cell sequencing (Vallejos, Risso, Scialdone, Dudoit, Marioni, 2017); SRS at $10^5$ samples has a drop-out rate of roughly 50%, evidence that SQUICH could significantly improve transcript detection in massive throughput single-cell sequencing. In summary, simulation shows that SQUICH exceeds performance of SRS by 100-1000 or more fold in diverse problems including detection of expression of rare species, small fold changes and quantifying species at high dynamic ranges.

SQUICH, as modeled in simulation, can be directly applied to primary biological samples whenever an orthogonal barcode is introduced into the sample, e.g. pooled chemical or genetic screens, with gains in sampling precision illustrated above. To test SQUICH in real next-generation sequencing experiments, a synthetic target library of complexity $2^{18}=262,144$, similar to the CGA code set was designed and a set of individual species ranging from 81× to 80,000× fold over background was manually added (Methods, Table S4-5). SQUICH was carried out with 10-fold increases in total molecules in each round, low encoder amounts in the first round and constant encoder amounts in rounds 2-6 (Methods). Six SQUICH libraries prepared with two levels of encoder in round one were sequenced to a mean depth of 2187 reads. Six conventional libraries that model SRS with experimental error introduced during library preparation were sequenced to a mean depth of 19759. In all SQUICH replicates, Pearson and rank correlation between ground truth and estimated abundance exceed all replicates of conventional libraries, despite SQUICH libraries being sequenced at >9-fold lower depth (Methods, FIG. 20).

To control for the high leverage of species with high abundance on correlation values, a conservative measure of performance of SQUICH vs. conventional sequencing using a rank based method was used (Methods). 3 of the 6 SQUICH runs sequenced exceeded performance of all 6 conventional sequencing experiments. In addition, 5 out of 6 replicates were statistically significantly more sensitive than SRS with no noise introduced during sequencing (p<0.05 in 5 out of 6 replicates; p=0.138 in one replicate, labeled CH52.03, Table S3). No p-values were significant for conventional experiments. A statistical method to control for variable sampling depths in SQUICH and conventional libraries was developed, and the method was used to estimate SQUICH efficiency compared to conventional sequencing; it also estimated that proof-of-principle SQUICH experiments achieves a 10× reduction in sequencing depth compared to conventional sequencing.

Discussion

MEG, and a specific example, SQUICH, is a new framework for quantifying each of a large number (millions or more) species of molecules in a pool, one of the most ubiquitous and important molecular measurement problems today. MEG theory can be applied to any molecular sampling problem, though here the focus was on DNA. Small molecules, proteins and RNA can be tagged with DNA sequences, so common assays and screens all reduce to SQUICH, and more generally MEG, measurement. In applications where the sample is limiting, such as biomedical testing, increasing sampling depth is impossible, as sample amplification introduces extra sources of measurement error. In these areas, MEG may be especially important. The flexibility of the sampling distribution provided by MEG expands the scope of statistical algorithms that can be used for estimation. Further, MEG provides key advantages when integrated with modern statistical approaches that use assumptions of sparsity to both improve precision in signal detection and reduce resource cost.

For example, SQUICH could be an ideal platform to measure massive single-cell RNA profiles. To illustrate the design of SQUICH for single-cell RNA-seq, a molecular mapping strategy to combine cell barcodes and gene identity into a single target code as a concise input into SQUICH was provided. Because this strategy involves hybridization, it has a further unique advantage to improve performance in single-cell applications: multiple target codes can be mapped to the same molecule (e.g. RNA) through hybridization in (FIG. S1) with the potential to reduce drop-out, resolve isoforms and overcome 3' bias or the requirement of a poly-A tail.

It is predicted that MEG's design enables even further sampling reductions by providing a platform to convert measurement of nucleic acids into target codes that can be measured by approaches such as compressed sensing, which is not possible achieved with traditional sequencing (Candès, 2006; Cleary, Cong, Lander, Regev, 2017). SQUICH and MEG enable experiment-specific sampling paradigms that lead to future sampling reductions, for example to measure molecules only when their abundance is above a prespecified value. In proof-of-principle SQUICH experiments achieves 10× reduction, it is foreseen that much greater fold reduction occurs by increasing hamming distance between sequences in the pool of targets, competitors and encoders, and increasing purity of oligosynthesis, and by experimental designs that enable specific sampling of only species exceeding or depleted by a prespecified fold. This can be achieved by SQUICH by varying the abundance of each competitor (or encoder) target-by-target, so that for example, either encoders in early rounds are omitted, resulting in only sampling species exceeding a fixed threshold, or increasing encoders in early rounds and decreasing competitors to sample species at low abundance more deeply (unpublished work). In summary, MEG is a new approach for overcoming fundamental limitations in molecular sampling and could enable a new generation of efficient, precise biochemical measurement, from screens to detection of rare species in the blood and single-cell sequencing at an unprecedented resolution, with large numbers of potential variations and platforms.

REFERENCES

Cleary, C., Cong, L., Lander, E., & Regev, A. (2017). Composite measurements and molecular compressed sensing for highly efficient transcriptomics. bioRxiv.

Vallejos, C. A., Risso, D., Scialdone, A., Dudoit, S., & Marioni, J. C. (2017). Normalizing single-cell RNA sequencing data: Challenges and opportunities. Nature Methods, 14(6), 565-571.

Zadeh, J. N., Steenberg, C. D., Bois, J. S., Wolfe, B. R., Pierce, M. B., Khan, A. R., . . . , Pierce, N. A. (2010). NUPACK: Analysis and design of nucleic acid systems. Journal of Computational Chemistry, 32(1), 170-173.

Candès, E. (n.d.). Compressive sampling. Proceedings of the International Congress of Mathematicians Madrid, Aug. 22-30, 2006, 1433-1452.

Gu, W., Crawford, E. D., O'Donovan, B. D., Wilson, M. R., Chow, E. D., Retallack, H., & Derisi, J. L. (2015). Depletion of Abundant Sequences by Hybridization (DASH): using Cas9 to remove unwanted high-abundance species in sequencing libraries and molecular counting applications.

Conway, J. H., & Sloane, N. J. (2011). Sphere packings, lattices and groups. New York: Springer.

Hubank, M., & Schatz, D. (1994). Identifying differences in mRNA expression by representational difference analysis of cDNA. Nucleic Acids Research, 22(25), 5640-5648.

Boone, M., De Koker, A., & Callewaert, N. (2018). Capturing the 'ome': The expanding molecular toolbox for RNA and DNA library construction. Nucleic Acids Research, 46(6), 2701-2721.

Wang, J. S., & Zhang, D. Y. (2015). Simulation-guided DNA probe design for consistently ultraspecific hybridization. Nature Chemistry, 7(7), 545-553.

Zhang, D. Y., Chen, S. X., & Yin, P. (2012). Optimizing the specificity of nucleic acid hybridization. Nature Chemistry, 4(3), 208-214.

Owczarzy, R., Tataurov, A. V., Wu, Y., Manthey, J. A., Mcquisten, K. A., Almabrazi, H. G., . . . , Peek, A. S. (2008). IDT SciTools: A suite for analysis and design of nucleic acid oligomers. Nucleic Acids Research, 36 (Web Server).

Sano, T., Smith, C., & Cantor, C. (1992). Immuno-PCR: Very sensitive antigen detection by means of specific antibody-DNA conjugates. Science, 258(5079), 120-122.

Robinson, M. D., & Smyth, G. K. (2007). Moderated statistical tests for assessing differences in tag abundance. Bioinformatics, 23(21), 2881-2887.

Mcintyre, L. M., Lopiano, K. K., Morse, A. M., Amin, V., Oberg, A. L., Young, L. J., & Nuzhdin, S. V. (2011). RNA-seq: Technical variability and sampling. BMC Genomics, 12(1).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. A method of sample analysis comprising:
   (a) obtaining a reagent system comprising:
      a plurality of oligonucleotide sets, each set comprising:
         i. a first detector oligonucleotide comprising a sequence that is complementary to a target sequence and a barcode that is 5' of the target-complementary sequence; and
         ii. a first competitor oligonucleotide that does not comprise the barcode and competes with the first detector oligonucleotide for binding to the target sequence;
      wherein:
         i. the concentration of the competitor oligonucleotide is different in each of the oligonucleotide sets; and
         ii. the barcode sequence is different in each oligonucleotide set and indicates the concentration of the first competitor oligonucleotide in the oligonucleotide set;
   (b) sequentially hybridizing the oligonucleotide sets of (a) with a sample that comprises a population of molecules that comprise the target sequence, wherein the oligonucleotide sets are hybridized in order of increasing concentration of the competitor oligonucleotide; and
   (c) quantifying the amount of each barcode in the detector oligonucleotides that hybridize to the population of molecules in step (b).

2. The method of claim 1, wherein (c) comprises performing a biochemical reaction on the hybridization products after each oligonucleotide set has hybridized and analyzing the reaction products.

3. The method of claim 2, wherein the biochemical reaction comprises: i. extending the hybridized target sequence using the detector oligonucleotides as a template, thereby producing primer extension products that comprise the complement of the barcodes of the hybridized detector oligonucleotides or ii. extending the hybridized detector oligonucleotides using the target sequence as a template, thereby producing primer extension products that comprise the barcodes of the hybridized detector oligonucleotides.

4. The method of claim 3, further comprising quantifying the amount of each barcode, or complement thereof, in the primer extension products.

5. The method of claim 1, wherein each oligonucleotide set is a separate mixture, and the method comprises:
   (a) hybridizing an aliquot of each mixture of oligonucleotides to the sample produce a hybridized sample;
   (b) performing the biochemical reaction on the hybridized sample of (a); and
   (c) repeating steps (a) and (b) using a different mixture of oligonucleotides, until all of the mixtures of oligonucleotides have been hybridized to the sample,
   wherein the mixtures of oligonucleotides used in steps (a) and (c) are added to the sample in order of increasing concentration of the competitor oligonucleotide.

6. The method of claim 1, wherein:
   all of the oligonucleotide sets in the plurality of oligonucleotides are mixed together with the sample in a reaction mix,
   the oligonucleotide sets that have a lower concentration of competitor oligonucleotide hybridize to their targets at a higher temperature than the oligonucleotide sets that have a higher concentration of competitor oligonucleotide, and
   the sequential hybridization of the plurality of oligonucleotide sets is done by lowering the temperature of the reaction mix.

7. The method of claim 1, wherein
   all of the oligonucleotide sets in the plurality of oligonucleotides are mixed together with the sample in a reaction mix,
   the oligonucleotide sets that have a lower concentration of competitor oligonucleotide hybridize to their targets faster than the oligonucleotide sets that have a higher concentration of competitor oligonucleotide, and
   the sequential hybridization of the plurality of oligonucleotide sets is done by incubating the reaction mix at a single temperature.

8. The method of claim 1, wherein the quantifying is done by sequencing, qPCR, or by hybridization to an array.

9. The method of claim 1, wherein the method comprises:
   determining the profile of barcode sequences in the products.

10. The method of claim 9, wherein the method comprises:
    quantifying the abundance of a nucleic acid comprising a target sequence in the sample based on the profile of barcode sequences or complements thereof.

11. A reagent system for nucleic acid analysis, comprising:
    a plurality of oligonucleotide sets each set comprising:
       i. a first detector oligonucleotide comprises a sequence that is complementary to a target sequence and a barcode that is 5' of the target-complementary sequence; and
       ii. a first competitor oligonucleotide that does not comprises the barcode and competes with the first detector oligonucleotide for binding to the target sequence;
    wherein:
       i. the concentration of the competitor oligonucleotide is different in each of the oligonucleotide sets; and
       ii. the barcode sequence is different in each oligonucleotide set and indicates the concentration of the first competitor oligonucleotide in the oligonucleotide set.

12. The reagent system of claim 11, wherein each oligonucleotide set is a separate mixture.

13. The reagent system of claim 11, wherein all of the oligonucleotide sets in the plurality are present in the same mixture.

14. The reagent system of claim 13, wherein, in the mixture, the oligonucleotide sets that have a lower concentration of competitor oligonucleotide have a higher Tm than the oligonucleotide sets that have a higher concentration of competitor oligonucleotide.

15. The reagent system of claim 11, wherein within each oligonucleotide oligonucleotide set the target-complementary sequence and the first competitor oligonucleotide have at least 15 contiguous nucleotides that are identical.

16. The reagent system of claim 11, wherein the concentrations of the competitor oligonucleotide are at least 2-fold different from oligonucleotide set to oligonucleotide set.

17. The reagent system of claim 11, wherein the detector oligonucleotide(s) are of formula p2–n–A', wherein A' hybridizes to the target sequence, n is the barcode and p2 provides a primer binding site.

18. The reagent system of claim 11, wherein the detector oligonucleotides are blocked at the 3' end.

19. A reagent system for nucleic acid analysis, comprising:
   a plurality of oligonucleotide sets, each set comprising:
   i. a first detector oligonucleotide, of formula n–$A_1$'; and
   ii. a first competitor oligonucleotide of sequence $A_1$';
      wherein:
         sequence $A_1$' of each first detector oligonucleotide and each first competitor oligonucleotide hybridizes to a first target sequence, of sequence $A_1$;
         the concentration of the competitor oligonucleotide is different in each of the oligonucleotide sets; and
         sequence n is a barcode sequence that is different in each oligonucleotide set and indicates the concentration of the first competitor oligonucleotide in the oligonucleotide set.

20. The reagent system of claim 19, wherein each oligonucleotide set further comprises:
   iii. a second detector oligonucleotide, of formula n–$A_2$'; and
   iv. a second competitor oligonucleotide, of sequence $A_2$';
      wherein:
         sequence $A_2$' of each second detector oligonucleotide and each second competitor oligonucleotide hybridizes to a second target sequence, of sequence $A_2$;
         sequences $A_1$ and $A_2$ are different; and
         sequence n is a barcode sequence that is different in each oligonucleotide set and indicates the concentration of the second competitor oligonucleotide in the oligonucleotide set.

\* \* \* \* \*